United States Patent [19]

Smulson et al.

[11] Patent Number: 5,449,605

[45] Date of Patent: * Sep. 12, 1995

[54] METHOD OF DETECTING A PREDISPOSITION TO CANCER BY DETECTING A DELETION POLYMORPHISM IN THE GENE FOR HUMAN POLY (ADP-RIBOSE) POLYMERASE

[75] Inventors: Mark E. Smulson; Deborah Lyn, both of Washington, D.C.; Barry Cherney, Arlington, Va.

[73] Assignee: Georgetown University, Washington, D.C.

[*] Notice: The portion of the term of this patent subsequent to Dec. 21, 2010 has been disclaimed.

[21] Appl. No.: 44,618

[22] Filed: Apr. 6, 1993

Related U.S. Application Data

[63] Continuation-in-part of Ser. No. 257,696, Oct. 14, 1988, Pat. No. 5,272,057.

[51] Int. Cl.6 .......... C12Q 1/68; C12P 19/34; C07H 21/02; C07H 21/04
[52] U.S. Cl. .......... 435/6; 536/23.2; 536/24.33; 435/91.2; 935/77; 935/78
[58] Field of Search .......... 435/6, 91.2, 91.1; 536/23.1, 24.33, 232

[56] References Cited

U.S. PATENT DOCUMENTS 4,379,839 4/1983 Spiegelman .......... 435/5
4,395,486 7/1983 Wilson et al. .......... 435/6
4,582,788 4/1986 Erlich .......... 435/6

(List continued on next page.)

FOREIGN PATENT DOCUMENTS 0229674 7/1987 European Pat. Off.

OTHER PUBLICATIONS

Bhatia et al., Cancer Res. 50:5406–5413 (Sep. 1, 1990).
Cherney et al., PNAS, USA 84:8370–8374 (Dec. 1987).
Kurosaki et al., J. Biol. Chem. 262 (33):15990–15997 (Nov. 25, 1987).
Skolnick et al., Genomics 2:273–279 (1988).
Suzuki et al., BBRC 146(2):403–409 (Jul. 3, 1987).
Uehida et al., BBRC 148(2):617–622 (Oct. 29, 1987).
Alkhatib, H. M. et al., Cloning and expression of cDNA for human poly(ADP-ribose) polymerase, Proc. Natl. Acad. Sci. USA 84:1224–1228 (Mar. 1987).
Benjamin, R. C. et al., Poly(ADP-ribose) Synthesis in Vitro Programmed by Damaged DNA, A Comparison of DNA Molecules Containing Different Types of Strand Breaks, J. Biol. Chem. 255(21):10502–10508 (Nov. 10, 1980).
Burzio, L. et al., Poly (Adenosine Diphosphoribose) Synthase Activity of Isolated Nuclei of Normal and Leukemic Leukocytes (38930), Proc. Soc. Exp. Biol. Med. 149:993–938 (1975).
Chatterjee, S. et al., Strategy for Selection of Cell Variants Deficient in Poly (ADP-Ribose) Polymerase, Experimental Cell Research 172:245–257 (1987).

(List continued on next page.)

Primary Examiner—Stephanie W. Zitomer
Attorney, Agent, or Firm—Sterne, Kessler, Goldstein & Fox

[57] ABSTRACT

The invention relates to a method for detecting the presence of a DNA deletion polymorphism associated with susceptibility for cancer in a human using allele specific amplification primers. Disclosed herein are methods for analyzing human DNA using a hybridization probe which will identify a restriction fragment length polymorphism within the 13q33→qter locus, methods for selectively amplifying DNA within this locus, methods of identifying and producing or purifying the peptide encoded by the human poly (ADP-ribose) polymerase processed pseudogene, and methods of regulating the expression of said processed pseudogene.

8 Claims, 21 Drawing Sheets

U.S. PATENT DOCUMENTS

| | | | |
|---|---|---|---|
| 4,699,877 | 10/1987 | Cline et al. | 435/6 |
| 5,085,983 | 2/1992 | Scanlon | 435/6 |
| 5,272,057 | 12/1993 | Smulson et al. | 435/6 |

OTHER PUBLICATIONS

Fukushima, M. et al., Poly(ADP-Ribose) Synthesis In Human Cervical Cancer Cell—Diagnostic Cytological Usefulness, *Cancer Letters* 14:227–236 (1981).

Harris, A. L., DNA repair: relationship to drug and radiation resistance, metastasis and growth factors, *Int. J. Radiat. Biol.* 48(5):675–690 (1985).

Hirai, K. et al., Aberration of Poly(Adenosine Diphosphate-Ribose) Metabolism in Human Colon Adenomatous Polyps and Cancer, *Cancer Research* 43:3441–3446 (Jul. 1983).

Holtlund, J. et al., A Comparison of Purified Poly(ADP-ribose) Polymerases from Ehrlich Ascites Tumor Cells, Pig Thymus, and HeLa S3 Cells, *Eur. J. Biochem.* 119:23–29 (1981).

Holtlund, J. et al., Poly(ADP-Ribose) Polymerase from Ehrlich Ascites-Tumour Cells, Amino Acid Composition, N-terminal Analysis and Chemical Cleavage of the Purified Protein, *Biochem. J.* 185:779–782 (1980).

Kasid, U. N. et al., Relationship between DNA strand breaks and inhibition of poly(ADP-ribosylation): enhancement of carcinogen-induced transformation, *Carcinogenesis* 7(2):327–330 (1986).

Kato, Y. et al., Restriction fragment length polymorphism of bcr in Japanese patients with hematological malignancies, *Leukemia* 2(10):701–703 (1988), *Biol. Abstr.* 87(1):AB-673, Abstract No. 6774.

Kristensen, T et al., Poly(ADP-ribose) Polymerase from Ehrlich Ascites Tumor Cells, *Eur. J. Biochem.* 88:495–501 (1978).

Lidereau, R. et al., Presence of an allelic EcoR1 restriction fragment of the c-mos locus in leukocyte and tumor cell DNAs of breast cancer patients, *Proc. Natl. Acad. Sci. USA* 82:7068–7070 (Oct. 1985).

Miwa, M. et al., Cell Density-Dependent Increase in Chromatin-Associated ADP-Ribosyltransferase Activity in Simian Virus 40-Transformed Cells, *Arch. Biochem. Biophys.* 181:313–321 (1977).

Mourelatos, D. et al., Synergistic induction of sister-chromatid exchanges in lymphocytes from normal subjects and from patients under cytostatic therapy by inhibitors of poly(ADP-ribose) polymerase and antitumour agents, *Mutation Research* 143:225–230 (1985).

Olzewska, E. et al., Somatic DNA variability in human breast carcinoma, *Oncogene* 1(4);403–408 (1987).

Paulsen, G. et al., Determination of the HLA-DR profile of an HLA class II negative carcinoma cell line by restriction fragment length polymorphism (RFLP) analysis, *Biol. Abstracts* 84(8):AB-429, Abstract No. 76620 (1987).

Pohl, A. L. et al., Enzyme Activities in Human Breast Tumor Cells and Sera, *Cancer Detection and Prevention* 8:57–66 (1985).

Scovassi, A. I. et al., Catalytic Activities of Human Poly(ADP-ribose) Polymerase from Normal and Mutagenized Cells Detected after Sodium Dodecyl Sulfate-Polyacrylamide Gel Electrophoresis, *J. Biol. Chem.* 259(17):10973–10977 (Sep. 10, 1984).

SenGupta, D. N. et al., Sequence of Human DNA Polymerase $\beta$ mRNA Obtained Through cDNA Cloning, *Biochem. Biophys. Res. Comm.* 136(1);341–347 (Apr. 14, 1986).

Slattery, E. et al., Purification and Analysis of a Factor Which Supresses Nick-induced Transcription by RNA Polymerase II and Its Identity with Poly(ADP-ribose) Polymerase, *J. Biol. Chem.* 258(9):5955–5959 (May 10, 1983).

Berger, N. A. et al., Association Of Poly(ADP-Ribose) Synthesis With DNA Strand Breaks In Replication And Repair, in Smulson and Sugimura, eds., Novel ADP-Ribosylations of Regulatory Enzymes and Proteins, *Developments in Cell Biology*, volume 6, Elsevier, pp. 185–195 (1980).

Sudhakar, S. et al., Effect of 1-Methyl-1-nitrosourea on Poly(Adenosine Diphosphate-Ribose) Polymerase Activity at the Nucleosomal Level, *Cancer Research* 39:1405–1410 (Apr. 1979).

Sugimura, T. et al., Poly(ADP-ribose) and cancer research, *Carcinogenesis* 4(12):1503–1506 (1983).

Suzuki, H. et al., Molecular Cloning of cDNA For Human Poly(ADP-Ribose) Polymerase And Expression Of Its Gene During HL-60 Cell Differentiation, *Biochem. Biophys. Res. Comm.* 146(2):403–409 (Jul. 31, 1987).

Uchida, K. et al., Nucleotide Sequence Of A Full-Length cDNA For Human Fibroblast Poly(ADP-Ribose) Polymerase, *Biochem. Biophys. Res. Comm.* 148(2):617–622 (Oct. 29, 1987).

(List continued on next page.)

OTHER PUBLICATIONS

Alberts, B. et al., *Molecular Biology of the Cell*, Garland Publishing, New York, pp. 470–471, (1983).

Compton, T., "Degenerate Primers For DNA Amplification," *PCR Protocols*, eds. Innis et al., Harcourt Brace Jovanovich, Publishers, pp. 39–45 (1990).

Durkacz, B. et al., "ADP-Ribose and DNA Repair," in: Novel ADP-Ribosylations of Regulatory Enzymes and Proteins, Proceedings of the Fogarty Intl. Conf. on Novel ADP-Ribosylations of Regulatory Enzymes and Proteins, eds. Smulson and Sugimura, Elsevier/North-Holland Publishers, pp. 207–216 (Oct. 22–24, 1979).

Erlich, H. & Bugawan, T., "HLA DNA Typing," *PCR Protocols*, eds. Innis et al., Harcourt Brace Jovanovich, Publishers, pp. 261–271 (1990).

Lyn, D. et al., "A Duplicated Region is Responsible for the Poly(ADP-ribose) Polymerase Polymorphism, on Chromosome 13, Associated with a Predisposition to Cancer," *Am. J. Hum. Genet.* 52:124–134 (1993).

Lyn, D. et al., "The Polymorphic ADP-Ribosyltransferase ($NAD^+$) Pseudogene 1 in Humans Interrupts an Endogenous pol–like Element on 13q34," *Genomics* 18:206–211 (1993).

Prins, J. et al., "The myc Family of Oncogenes and their Presence and Importance in Small-Cell Lung Carcinoma and Other Tumour Types," *Anticancer Research* 13:1373–1386 (1993).

Service, R., "Slow DNA Repair Implicated In Mutations Found in Tumours," *Science* 263:1374 (Mar. 11, 1994).

Skidmore, et al., "Poly(ADP-Ribose) Polymerase—An Enzyme Sensitive to DNA Damage," in: *Novel ADP-Ribosylations of Regulatory Enzymes And Proteins*, Proceedings of the Fogarty Int. Conf. on Novel ADP-Ribosylations of Regulatory Enzymes and Proteins, eds. Smulson and Sugimura, pp. 197–205 (Oct. 22–24, 1979).

```
  1   AAGCTTGAAAAGGCCCTAAAGCCCAGAACGACCTGATCTGGAACATCAA    A allele
        |||||||||||||||||||||||||| ||||||||||||||||||||||
887   AAGCTTGAAAAGCCCCTAAAGCTCAGAACGACCTGATCTGGAACATCAA    cDNA 51   GGACGAGCTAATGAAAGTGTGCTCTATTAATGACCTGAAGGAGATGCTCA    A allele
        ||||||||||| |||||||||| ||| |||||||||||||||| |||||
937   GGACGAGCTAAAGAAAGTGTGTTCAACTAATGACCTGAAGGAGCTACTCA    cDNA 101   TCTTCAACAGGCAGCAGGTGCCTTCCGGGGAGTCGGCGATCTTGGACCGA    A allele
        ||||||||| ||||||||| ||||||| ||||||||||||||||||| |
 98   TCTTCAACAAGCAGCAGGTACCTTCTGGGAGTCGGCGATCTTGGACCGA    cDNA 151   GTAGCTGACAGCATGACGTTCGGTGCCCTCCCTTCCCTGTGAGGAATGCTC    A allele
        ||||||||| |||| ||| ||||  ||||||||||||||||||||||||
1037  GTAGCTGATGGCATGGTGTTCGGTGTTCGGTGCCCTGCGAGGAATGCTC    cDNA 201   AGGTCAGCTGGTCTTCAAGAGCGACACTTATTACTGCACCGGGGACGTCA    A allele
        |||||||||| ||||||||||  ||||| ||||||||||| || ||| |
1087  GGGTCAGCTGGTCTTCAAGAGCGATGCCTATTACTGCACTGGGGACGTCA    cDNA
```

FIG.2A

```
251   CGGCCTGGACCAAGTGTATGGTCAAGACATGGACACCCAACCAGAAGGAA    A allele
      - |||||||||||||||||||||||||| |||||||  ||||||||||| 
1137  CTGCCTGGACCAAGTGTATGGTCAAGACACAGACACCCGGAAGGAG       cDNA 301   TAGGTGATCCCA........CCGAGAAATCTTAACTCAAGAAATTTAA     A allele
       ||| | ||||          |||||||||||  ||||||||||| || 
1187  TGGGTAACCCCAAAGGAATTCCGAGAAATCTCTTACCTCAAGAAATTGAA   cDNA 343   GGTTAAAAAGCAGGACCGTATATTCCCCCAGAAACCAGTGACCCAGTGG    A allele
      |||||||||||||||||||||||||||||||||||||||| ||| |||| 
1237  GGTTAAAAAGCAGGACCGTATATTCCCCCAGAAACCAGCCCTCCGTGG     cDNA 393   CGGCCATGCCCCCACCCTCCACAGCCTCCGAGCCTGCCATGAACGCC      A allele
      ||||| ||| ||| |||||||||||||||||||||||||| |||||  
1287  CGGCCACGCGCCCCGCCCTCCACAGCCTCCGGCTCCTGCTGTGAACTCC    cDNA 443   TCTGCTCCAGCAGATAAGCCGTTATCCAACATGAAGATCCTTACTCTTGG   A allele
      ||||| || |||||||||||| |||||||||||||||||||| || ||| 
1337  TCTGCTTCAGCAGATAAGCCATTATCCAACATGAAGATCCTGACTCTCGG   cDNA
```

FIG. 2B

```
 493 GAAGCTCTCCCGGAACAAGGATGAAGTGAAGGCCACGATTGAGAAACTCG     A allele
     ||||| || ||||||||||||||| ||||||||||||| |||||||||||
1387 GAAGCTGTCCCGGAACAAGGATGAAGTGAAGGCCATGATTGAGAAACTCG     cDNA 543 GGGGAAAGTTGATGGGGACGGGCCAACAAGGCTTCTCCGTGCATCAGCACT     A allele
     |||| |||||| || ||||||||||||||||||||| ||||||||||||||
1437 GGGGGAAGTTGACGGGGACGGGCCAACAAGGCTTCCCTGTGCATCAGCACC     cDNA 593 AAAGAGGAGGTGGAAAAGAGAAGAAGAAGATGGAGGAAGTGAAAGAAGC     A allele
     ||| ||||||||||||| ||||||||  ||| ||||||||||| |||||||
1487 AAAAAGGAGGTGGAAAAGAGAATAAGAAGATGGAGGAAGTAAAGGAAGC     cDNA 643 CAACATCTGAGCTGTGTCTGAGGACTTCCTCCAGGACTTCTCTGCCTCCA     A allele
     |||||||| ||||| || |||||||||||||||||||||| | ||||||
1537 CAACATCCGAGTTGTGTCTGAGGACTTCCTCCAGGACGTCTCCGCCTCCA     cDNA 693 CCAAGGGGCTCCAGGAGTTGTTCTCAGCGGCACATATTGACCCCCTGGGGG     A allele
     |||| |||||||||||||||||||| |||||||||| |||||||| ||||
1587 CCAAGAGCCTTCAGGAGTTGTTCTTAGCGGCACATCTTGTCCCCTTGGGGG     cDNA
```

FIG. 2C

```
743  GCAGAGGTGAAGGCAGAGCCTGTTGAAGTCGTAGCCCCAAGAGGGAAGTC    A allele
     ||| |||||||||||||||||||||||||||| ||||||||||||||||
1637 GCAGAGTGAAGGCAGAGCCTGTTGAAGTCGTGTGGCCCCAAGAGGGAAGTC   cDNA 793  AGGAGCTGTGCTCTCCAAAAAAGCAAGGGCCAGGTCAAGGAGGAAGGTA     A allele
     |||||||| ||||||||||||||||||||||||||||||||||||||||
1687 AGGGGCTGCGCTCTCCAAAAAAGCAAGGGCCAGGTCAAGGAGGAAGGTA     cDNA 843  TCAACAAATCTGAAAAGAGAATGAAATTAACTCTTAAAGGAGGAGCAGCT    A allele
     |||||||||||||||||||||||||||||||||||||||||||||||||
1737 TCAACAAATCTGAAAAGAGAATGAAATTAACTCTTAAAGGAGGAGCAGCT    cDNA 893  GTGGATCCTGACTCTCGGTCTCTGGAACACTCTGCGCATGTCCTGGAGAAAGG A allele
     ||||||||||| |||| ||||||||||||||||||| |||||||||||||
1787 GTGGATCCTGATTCTCGATTCTGGAACACTCTGCGGCATGTCCTGGAGAA... cDNA 943  TGAAGGCAGAGCCTGTTGAAGTCGTAGCCCCAAGAGGGAAGTCAGGAGCT    A allele
```

FIG. 2D

```
993  GTGCTCTCCAAAAAGCAAGGGCCAGTCAAGGAGGAAGGTATCAACAA                          A allele 1043 ATCTGAAAAGAGAATGAAATTAACTCTTAAAGGAGGAGCAGCTGTGGATC                        A allele 1093 CTGACTCTGGTCTGGAACACTCTGCACATGTTCTGGAGAAAGGTGGGAAG                        A allele
     ||||||||||||||                                     |||||||||
1826                                                   AGGTGGGAAG           cDNA 1143 GTCTTCAGTGCCACCCTCAGCCTGGTGGCCTGGTGACGTCGTTAAAGGAACCAACTC                A allele
     ||||||||||||||||||||||||||||||||||||||| |||||||||||||||||
1844 GTCTTCAGTGCCACCCTCAGCCCTGGTGGCCTGGTGACATCGTTAAAGGAACCAACTC               cDNA 1193 CTATTACAAGCTGAAGTTGCTGAAGGATGACAAGGAAAGCAGGCATTGGA                       A allele
     || |||||||||||||||||||| |||| |||||  |||||||||| |||
1894 CTACTACAAGCTGCAGCTTCTGGAGGACGACAAGGAAAACAGGTATTGGA                       cDNA
```

FIG. 2E

```
1243  TATTCAAGTCCTGGGACCGTGTGGGCACGGTGATCGGTAGCAACAAACTG  A allele
      ||||||||||||||| |||||||||||||||||||||||||||||||||
1944  TATTCAGGTCCTGGGGCCGTGTGGGTACGGTGATCGGTAGCAACAAACTG  cDNA 1293  GAACAGATGCTGTCCAAGGAGGACACCATTGAACACTTCATGAAATTATA  A allele
      ||||||||||||||||||||||||| ||||||||| ||||||||||||||
1994  GAACAGATGCCGTCCAAGGAGGATGCCATTGAGCAGTTCATGAAATTATA  cDNA 1343  TGAAG.AAAAACTAGGAATGCTTGGCACTCCAAAAA.TTCACAAAGTATC  A allele
      ||||| |||| ||  ||  ||||||||||||||||| |||| ||||||||
1994  TGAAGAAAAAACCGGGAACGCTTGGCACTCCAAAAATTTCACGAAGTATC  cDNA 1391  CCAAAAAGTTCTACCCCCTGGAGATTGACTACGGCCAGGACAAAGAGGCG  A allele
      ||||||||||  |||||||||||||||||||| |||||||||| |||| 
2094  CCAAAAAGTTTTACCCCCTGGAGATTGACTATGGCCAGGATGAAGAGGCA  cDNA 1441  GTGAAGAAGCCGACAGTAAATCCTGGCACCAAGTCCATGCTCCCCAAGCC  A allele
      |||||||||||||||||||||||||||||||||||| |||||||||||||
2144  GTGAAGAAGCTCACAGTAAATCCTGGCACCAAGTCCAAGCTCCCCAAGCC  cDNA
```

FIG.2F

```
1491  AGTTCAGGACCTCATCAAGATGATCTTTGATGTGGAAAGTATGAGCAAAG    A allele
      ||||||||||||||||||||||||||||||||||||||||||||||||||
2194  AGTTCAGGACCTCATCAAGATGATCTTTGATGTGGAAAGTATGAAGAAAG    cDNA 1541  CCATGGTGGGGTGTGAGATCAACCTTC...AGATGCCCTTGGGGAAGCTG    A allele
      ||||||||||  ||  ||      ||     ||||||||||||||||||||
2244  CCATGGTGGAGTATGAGATCGACCTTCAGAAGATGCCCTTGGGGAAGCTG    cDNA 1588  AGCAAAAGGCAAATCCAGGCCGCGTACTCCATCCTC.....AGGTCCAGCA   A allele
      ||||||||||   |||||||||  ||||||||||||     ||||||||||
2294  AGCAAAAGGCAGATCCAGGCCGCCATACTCCATCCTCCAGTGAGGTCCAGCA  cDNA 1634  GGTGGTGTCCCAGGGCAGCAGCAGCAGACTCTCCAGATCCTGGATCTCTCAAATC  A allele
      |||||| ||||||||||||||||||||||||||||||||||||||||||||||
2344  GGCGGTGTCTCAGGGCAGCAGCAGCAGACTCTCCAGATCCTGGATCTCTCAAATC  cDNA 1684  GCTTTTACATCCCTGATCCCCCACGACTTTGGGATGAAGGATCCTCTGCTC   A allele
      ||||||||| |||||||||||||||||||||||||||   ||||||| ||
2394  GCTTTTACACCCCTGATCCCCCACGACTTTGGGATGAAGAAGCCTCCGCTC   cDNA
```

FIG. 2G

```
1734 CTGAACAATGCAGACAGTGTGCAGGCCAAGGTAGAAATGCTGGACAACCT    A allele
     |||||||||||||||||||||||||||||||||||||  ||||||||||
2444 CTGAACAATGCAGACAGTGTGCAGGCCAAGGTGGAAATGCTTGACAACCT    cDNA 1784 GCTGGACATTGAGGTAGCCTACGGTCTGCTCAGGGGAGGGTCTCACGATA    A allele
     ||||||||| || ||||  |||||||||||||||||||||||| |||||
2494 GCTGGACATCGAGGTGGCCTACAGTCTGCTCAGGGGAGGGTCTGATGATA    cDNA 1834 GCAGGAAGGACTCCATCGATGTCAACTATGAGAAGCTCAAAACTGACATT    A allele
     |||| |||| ||||| ||||||||||||||||||||||||||||||||||
2544 GCAGCAAGGATCCCATCGATGTCAACTATGAGAAGCTCAAAACTGACATT    cDNA 1884 AAGGTGGTTGACAGAGATTCTGAAGAAGCTGAGATCATCAGGAAGTATGT    A allele
     |||||||||||||||||||||||||||||||||||||||||||||||||||
2594 AAGGTGGTTGACAGAGATTCTGAAGAAGCCGAGATCATCAGGAAGTATGT    cDNA 1934 TAAGAACACTCATGCAACCAACCACCACACGATGCGCATATGACTTGGAAGTC    A allele
     ||||||||||||||            ||||||||||||||||||||||||
2644 TAAGAACACTCATG....CAACCACACAGTGCGTATGACTTGGAAGTC    cDNA
```

FIG. 2H

```
1984  ATTGATAGCTTTAAGATAGAGTGTGAAGAGGAGTGCCAGCACTACAAGCC   A allele
      || ||| ||||||||||||| ||||||| ||||||| ||||| ||||||||
2690  ATCGATATCTTTAAGATAGAGCGTGAAGGCCGAATGCCAGCCGTTACAAGCC  cDNA 2034  CTTAAGCAGCTTCATAACTGAAGGTTGCTGTGGCATGGGTCCAGGACCA   A allele
      ||||||||||||||||| ||||||||||||||| ||||||||||||||||
2740  CTTAAGCAGCTTCATAACCGAAGATTGCTGTGGCACGGGTCCAGGACCA   cDNA 2084  CCAACTTGCTGGGATCCTGTCCCTGGGTCTTTGGATAGCCCTGCCTGAA   A allele
      |||||||||||||||||||||||||||||||||||| |||||||||||||
2790  CCAACTTGCTGGGATCCTGTCCCAGGGTCTTCGGATAGCCCCGCCTGAA   cDNA 2134  GCACCTGTGATGGGCTACATGTTTGGTAAAGTGATCTCTATTTCGCTGATCT   A allele
      || |||   ||| ||| |||||||||||||||||||| ||||||||||||| |
2840  GCGCCCCGTGACAGGCTACATGTTTGGTAAAGGGATCTATTTCGCTGACAT   cDNA 2184  TGTCTCCAAGAGTGCCAACGACTGCCATACATCTTAGGAAGACCCAATAG   A allele
      || ||||||||||||||||| |||||||    | ||||| ||||||||||
2890  GGTCTCCAAGAGTGCCAACTACTACCATACGTCTCAGGGAGACCCAATAG  cDNA
```

FIG. 21

```
2234  GGTTAATCCTGTCGGAAGAAGTTGCCCTTGGAAACGTGTGTGAACTGAAG   A allele
      |||||  ||||||| |||||||||||||||||||| ||| |||||||||||
2940  GCTTAATCCTGTTGGGAGAAGTTGCCCTTGGAAACATGTATGAACTGAAG   cDNA 2284  CATGCTTCACATATCAGCAGTCAAGTTACCCAAGGGCAAGCACAGTGTCAAAGG   A allele
      | ||||||||||||||||||||| ||||||||||||||||||||||||||||||
2990  CACGCTTCACATATCAGCAGTTACCCAAGGGCAAGCACAGTGTCAAAGG       cDNA 2334  TTTGGGCAAAACTACTCCTGACCCTTTCAGCTAGTATCCCACTGGATGGTG   A allele
      ||||||||||||| || |  ||| ||||||||| |||||||| ||||||||
3040  TTTGGGCAAAACTACCCCCTGATCCTTCAGCTAACATTAGTCTGATGGTG     cDNA 2384  TAGAGGTTCCTCTTGGGACCAGGGTTTCATCTGGTGTGAATGACACCTGT   A allele
      ||| |||||||||||||||| |||||||||||||||||||||||||||| 
3090  TAGACGTTCCTCTTGGGACCGGGATTTCATCTGGTGTGAATGACACCTCT   cDNA 2434  CTACTGTATAATGAGTACATTGTCTATGATATTGCTCAGGTAAATCTGAA   A allele
      ||||| ||||| ||||||||||||||||||||||||||||||||||||||
3140  CTACTATATAACGAGTACATTGTCTATGATATTGCTCAGGTAAATCTGAA   cDNA
```

FIG. 2J

```
2484  ATATCTGCTGAAACTGAATTTCAATTTTAAGACCTCCCTTGTGGTAATTGG    A allele
      ||||||||||||||||||||||||||||||||||||||||||  |||||||
3190  GTATCTGCTGAAACTGAATTTCAATTTTAAGACCTCCCTGTGGTAATTGG    cDNA
                                                  ***

2534  GAGAGGTGGCTGAGTCACACACGGTGACTCTGGTATTAATTCACCCTAAG    A allele
      ||||||||| ||||||||||||||||| |||||| || ||||||| |||
3240  GAGAGGTAGCCGAGTCACACCCGGTGGCTGTGTATGAATTCACCCGAAG    cDNA 2584  CGCTTCTGCACCAACTCACCTGGCTAAGTTGCTGGTGGGTAGTACC    A allele
      |||||||||||||||||||||||  ||||||||||||||||||||
3290  CGCTTCTGCACCAACTCACCTGGC.CGCTAAGTTGCTGATGGGTAGTACC    cDNA 2634  TGTACTAAACCTCCTCAGAAAGGATTTTGCAGAAATGCATTAGAAGCTT    A allele
      |||||||||| ||||||||||||||||||| ||||| ||||| |||||
3339  TGTACTAAACCACCTCAGAAAGGATTTTACAGAAACGTGTTAAAGGTTT    cDNA
```

FIG. 2K

```
747   AGGTGAAGGC AGAGCCTGTT GAAGTCGTAG CCCCAAGAGG GAAGTCAGGA    Region 1 A allele
940   ..A.......  ..........  ..........  ..........  ..........    Region 2 A allele
1     ..........  ..........  .....T..G.  ..........  ..........    B allele
1641  ..........  ..........  ..........  ..........  .......G.    cDNA 797   GCTGTGCTCT CCAAAAAAAG CAAGGGCCAG GTCAAGGAGG AAGGTATCAA    Region 1 A allele
990   ..........  ..........  ..........  ..........  ..........    Region 2 A allele
51    ...C......  ..........  ..........  ..........  ..........    B allele
1691  ..........  ..........  ..........  ..........  ..........    cDNA 847   CAAATCTGAA AAGAGAATGA AATTAACTCT TAAAGGAGGA GCAGCTGTGG    Region 1 A allele
1040  ..........  ..........  ..........  ..........  ..........    Region 2 A allele
101   ..........  ..........  ..........  ..........  ..........    B allele
1741  ..........  ..........  ..........  ..........  ..........    cDNA 897   ATCCTGACTC TGGTCTGGAA CACTCTGCGC ATGTCCTGGA GAA           Region 1 A allele
1090  ..........  ..........  .......A..  ....T.....  ...          Region 2 A allele
151   ..........  ...T......  .......A..  ....T.....  ...          B allele
1791  ..........  ..........  ..........  ..........  ...          cDNA
```

FIG. 4

```
 925
GCATGTCCTGGAGAAAGGTGAAGGCAGAGAGCCTGTTGAAGTCGTAGCCCCAAGAGGGAAGT
 M  S  W  R  K  V  K  A  E  P  V  E  V  V  A  P  R  G  K  S

985
CAGGAGCTGTGCTCTCCAAAAAAAAGCAAGGGCCAGGTCAAGGAGGAAGGTATCAACAAAT
 G  A  V  L  S  K  K  S  K  G  Q  V  K  E  E  G  I  N  K  S

1045
CTGAAAAGAGAATGAAATTAACTCTCTTAAAGGAGGAGCAGCTGTGGATCCTGACTCTGGTC
 E  K  R  M  K  L  T  L  K  G  G  A  A  V  D  P  D  D  S  G  L

1105
TGGAACACACTCTGCACATGTTCTGGAGAAAGGTGGGAAGGTCTTCAGTGCCACCCTCAGCC
 E  H  S  A  H  V  V  L  E  K  G  G  K  V  F  S  A  T  L  S  L
```

FIG.6A

1165 TGGTGGACGTCGTTAAAGGAACCAACTCCTATTACAAGCTGAAGTTGCTGAAGGATGACA
V D V V K G T N S Y Y K L K L L K D D K

1225 AGGAAGCAGGCATTGGATATTCAAGTCCTGGGACCGTGTGGGCACGGTGATCGGTAGCA
E S R H W I F K S W D R V G T V I G S N

1285 ACAAACTGGAACAGATGCTGTCCAAGGAGGACACCATTGAACACTTCATGAAATTATATG
K L E Q M L S K E D T I E H F M K L Y E

1345 AAGAAAAACTAGGAATGCTTGGCACTCCAAAAATTCACAAAGTATCCCAAAAAGTTCTAC
E K L G M L G T P K I H K V S Q K V L P

1405 CCCCTGGAGATTGA
P G D *

FIG. 6B

|  | A | | B | | C | | D | | E |
|---|---|---|---|---|---|---|---|---|---|
|  | * *** * | | ** * ** * ****** * | | * ****** | | *** | |  |
| pol-like | KHKWFSIVDLKDAFWPC | [23] | RYHNTVLPQVFTESPKLTWSSLRKSSG | [10] | LLQYVDDLLIS | [19] | EKGLRVSKTKSQ | [4] | VKYLGHLISEG |
| RTVL-1 | NHQMFTVIDLKDAFNAC | [23] | NYQWTVLPQGFMESPNLFGQILEQVLD | [9] | LLQYVDDILLA | [19] | FEGLRVSKGKLQ | [5] | VKYLGRLISAG |
| 4-1 | EDSWFTCLDLKDAFFSI | [23] | QYYWTQLPQRFKNSPTIFGEALARDLQ | [10] | LLQYVDDLLLG | [19] | TVGIRCPRKKAQ | [5] | VCYLGFTIQQG |
| MoMLV | SHQWYTVLDLKDAFFCL | [23] | QLTWTRLPQGFKNSPTLFDEALHRDLA | [10] | LLQYVDDLLLA | [19] | NLGYRASAKKAQ | [5] | VKYLGYLLKEG |

FIG. 9

METHOD OF DETECTING A PREDISPOSITION TO CANCER BY DETECTING A DELETION POLYMORPHISM IN THE GENE FOR HUMAN POLY (ADP-RIBOSE) POLYMERASE

Part of the work leading to this invention was made with U.S. Government funds. The U.S. Government has certain rights in this invention.

RELATED APPLICATIONS

This application is a continuation-in-part application of U.S. Ser. No. 07/257,696, filed Oct. 14, 1988, now U.S. Pat. No. 5,272,057, issued Dec. 21, 1993.

FIELD OF THE INVENTION

This invention relates to methods of detecting a predisposition for cancer. The methods are based on the identification of restriction fragment length polymorphism within the DNA sequences for the pseudogene for human poly (ADP-ribose) polymerase using a hybridization probe and PCR amplification procedures.

BRIEF DESCRIPTION OF THE BACKGROUND ART

Carcinogenesis is a multistep process initiated by DNA damage, gene mutation, gene rearrangement and gene translocation, and ending with phenotypic transformation of cancer cells. Bishop, *Science* 235:305–311 (1987).

It is well documented that normal cellular genes ("proto-oncogenes") can be converted into oncogenes or cancer genes due to agents which cause DNA strand breaks and damage. Kasid, et al. *Carcinogenesis*, 7:327–330 (1986). Often, conversion involves the breakage of the proto-oncogene from DNA and its movement and placement through another break into another chromosome. Also, it is known that proto-oncogenes can become activated to become malignant oncogenes by gene amplification. Stark et al., *Ann. Rev. Biochem.* 53:447–491 (1984).

Most living cells possess systems tier recognizing and eliminating DNA damage. For example, the prokaryote, *E. coli*, possesses a variety of enzymes for responding to DNA damage. Such enzymes include those of the SOS repair system and various Rec proteins. These enzymes, and others, respond to DNA damage caused by U.V. radiation, chemical mutagens and the like. Eukaryotic and mammalian cells also possess DNA repair enzymes.

One mammalian enzyme, poly (ADP-ribose) polymerase, appears to play an important role in recovery of cells from DNA strand-breaking events. It has been reported that poly (ADP-ribose)polymerase activity is higher in isolated nuclei of SV 40 transformed fibroblasts than in those of untransformed fibroblasts; that leukemic cells showed higher enzyme activity than normal leukocytes; and that colon cancers showed higher enzyme activity than normal colon mucosa. Miwa et al., *Arch. Biochem. Biophys.* 181:313–321 (1977); Burzio et al., *Proc. Soc. Exp. Biol. Med.* 149:933–938 (1975); Hirai et al., *Cancer Res.* 43:3441–3446 (1983). It was concluded in these reports that the activity of the poly (ADP-ribose) polymerase responds to DNA damage and parallels DNA repair. It has also been reported that the reduction of activity of poly (ADP-ribose) polymerase by drugs increases DNA amplification and consequent oncogenesis in cells. Harris, *Int. J. Radiat. Biol.* 48:675–690 (1985).

In recent years, much work has centered around the exact mechanism by which poly(ADP-ribose)polymerase modulates the DNA replication/repair processes of mammalian cells. Berger et al., pp. 185–195 in Smulson and Sugimura, eds., "Novel ADP-Ribosylations of Regulatory Enzymes and Proteins," Elsevier, N.Y. (1980). It is known that this enzyme is a 113 kDa protein which uses NAD as a substrate in the formation of poly (ADP-ribose) polymerase chains at sites on many nuclear proteins. The enzyme binds tightly to DNA and requires DNA strand breaks for enzymatic activity. Benjamin et al., *J. Biol. Chem.* 255:10502–10508 (1980). It has been hypothesized that the enzyme system functions in response to transient and localized DNA strand breaks in cells that may arise through a variety of processes including DNA repair, replication, recombination and gene rearrangement. Alkhatib et al., *PNAS USA* 84:1224–1228 (1987). One reference has taught the measuring of the activity of this enzyme as a method of detecting a predisposition to cancer. Pero, European Patent No. 229,674, published Jul. 22, 1987.

In order to more precisely define the role of poly (ADP-ribose) polymerase, the gene for this enzyme has been sequenced and cloned and localized. Kurosaki et al., *J. Biol. Chem.* 262:15590 (1987) describes the sequence of cDNA clones representing most of a 4.9 kb mRNA for human poly (ADP-ribose) synthetase from transformed human fibroblasts. The investigators showed the restriction endonuclease map for the cloned cDNAs which reveals two Hind III sites and one Pst I site.

In Cherney et al., *Proc. Natl. Acad. Sci.* (USA) 84:8370 (December 1987), two of the present inventors and co-authors disclose the first intact cloned cDNA sequence of human poly (ADP-ribose) polymerase. They also disclosed the restriction endonuclease map with two Pst I sites and two Hind III sites. RLFP analysis was done on normal individuals' lymphocytes and fibroblast cell lines to determine chromosome location and two Hind III allele polymorphism were observed on chromosomes in samples from normal patients. It was concluded that the active and expressed gene was on human chromosome one and the processed pseudogene was on chromosome 13.

Thus, the recent cloning of the cDNA for the nuclear enzyme poly (ADP-ribose) polymerase allowed for subsequent derailed sequence analysis of this nuclear protein as well as detailed human chromosomal localization and initial characterizations of the polymorphism of this gene in the normal human population.

A restriction fragment length polymorphism (RFLP) of PADPRP-related sequences was identified and found to correlate with endemic Burkitts lymphoma, B cell follicular lymphoma and lung carcinoma (Bhatia et al., *Cancer Res.* 50:5406–5413 (1990)). A simple two allele (A/B) polymorphism localized to chromosome 13q33->qter was noted, in which the frequency of the B allele showed a two to three fold increase when tumor DNA were compared to a non-cancer population (Bhatia et al., *Cancer Res.* 50:5406–5413 (1990)).

The RFLP was identified by a Hind III 2.7-2.5 kb allelic combination using a human PADPRP cDNA as a probe, and was thought to be either a processed PADPRP pseudogene or a gene with extensive identity to PADPRP. Furthermore, the RFLP did not reflect the gene encoding the authentic PADPRP protein which occurs on chromosome 1 q or the pseudogene on chromosome 14 (Cherney et al., *Proc. Natl. Acad. Sci. USA* 84:8370–8374 (1987)). A preliminary characterization of this simple two allele (A/B) polymorphism showed that a number of other restriction enzymes including Kpn I, Eco RI, Bgl III, Rsa I and Msp I also identified this polymorphism which always cosegregated together and differed by 200 base pairs (bp) between the respective A and B alleles. Collectively, these RFLP's suggested a deletion or insertion of DNA of at least 200 bp adjacent to, or within PADPRP-like sequences.

In the initial study, analysis of DNA derived from tumor and normal tissue of the same individual revealed that the predominant source of this polymorphism was germline (Bhatia et al., *Cancer Res.* 50:5406–5413 (1990)). In addition, a tumor derived loss of heterozygosity was noted in 5% of the matched samples, and was not related to a deletion of the retinoblastoma gene (13q14) or other regions of the q arm of chromosome 13. In the noncancer population, a marked difference in the frequency of the B allele was also observed in germline DNA between racial groups (0.14 for whites and 0.35 for blacks). Moreover, an increased frequency of the B allele was still observed in tumor DNA compared to the racially appropriate noncancer germline DNA.

To provide insight into the association between the PADPRP polymorphism on chromosome 13 and a possible predisposition to cancer, we extended the previous survey by studying the B allele frequency from germline derived DNA in a new group of patients with cancers which occur more frequently in the black population (multiple myeloma, prostate and lung cancer). The genomic structure of the polymorphic PADPRP sequences was characterized by cloning and sequencing the Hind III allelic fragment. This report presents data which indicate that the polymorphism reflects a 193 bp duplication of PADPRP processed pseudogene sequences on chromosome 13. In addition, a strategy was developed to analyze the PADPRP genotype of patients using the polymerase chain reaction (PCR), in which the DNA sequences responsible for the A/B polymorphism could be selectively amplified.

SUMMARY OF THE INVENTION

The invention relates to methods for detecting the presence of a DNA polymorphism associated with susceptibility for cancer in a human. In one embodiment, the method involves analyzing human DNA using a hybridization probe which will hybridize to sequences encoding, or complementary to the pseudogene of human poly (ADP-ribose) polymerase wherein the probe is capable of identifying a restriction polymorphism. In another embodiment, allele specific amplification primers are described which are capable of distinguishing between the A and B allele of the pseudogene located on chromosome 13.

The invention is further based on the observation that the pseudogene on chromosome 13 contains an open reading frame which is capable of being transcribed and translated into a unique peptide. Utilizing this observation, 1) antibodies are described which are capable of binding to this peptide, 2) methods for detecting a predisposition for and the progression of tumors based on identifying the peptide are described, 3) agents (toxin derivatized antibodies) are described for selectively killing cells expressing this peptide, and 4) methods are described for selectively inhibiting the expression of this peptide based on anti-sense gene expression technology.

DESCRIPTION OF THE FIGURES

FIG. 2: Alignment of the PADPRP Hind III clone (A allele) to the cDNA. The upper sequence represents the complete sequence of the isolated A allele (chromosome 13) (SEQ ID NO. 3) while the lower sequence is the cDNA (derived from chromosome 1) as reported by Cherney et al., *Proc. Natl. Acad. Sci. USA* 84:8370–8374 (1987)(SEQ ID NO. 5). Sequence matches are shown by vertical lines. The overlined region corresponds to the oligonucleotide primers used in the PCR; the plus (+) overlined area represents sequences at the start and flanking the 3' end of the duplicated region while (***) indicates the protein termination codon of the cDNA which encodes the authentic PADPRP protein.

FIG. 4: Comparison of the duplicated PADPRP sequences of the A allele to the corresponding region on the cDNA. The 193 bp duplicated sequences from the A allele were taken from FIG. 2 (region 1 is nts 747–939 and region 2 is 940–1132)(SEQ ID NO. 3), while the cDNA was from Cherney et al., *Proc. Natl. Acad. Sci. USA* 84:8370–8374 (1987)(SEQ ID NO. 3). The sequence of the PCR product (B allele) was obtained from the reaction shown in lane 3, FIG. 5. Only non-identical nucleotides are indicated.

FIG. 6: The predicted amino acid sequence (SEQ ID NO. 6) of the potential open reading frame (ORF) in the cloned Hind IIIA allele. The nucleotide sequence shown includes nts 925 to 1418 from FIG. 2 (SEQ ID NO. 3). The underlined amino acids are homologous to the C-terminal portion of the automodification domain in the authentic PADPRP protein (Cherney et al., *Proc. Natl. Acad. Sci. USA* 84:8370–8374 (1987)).

FIG. 9: Sequence homology of the pol-like element to other known proteins

DETAILED DESCRIPTION OF THE INVENTION

Figure 1:
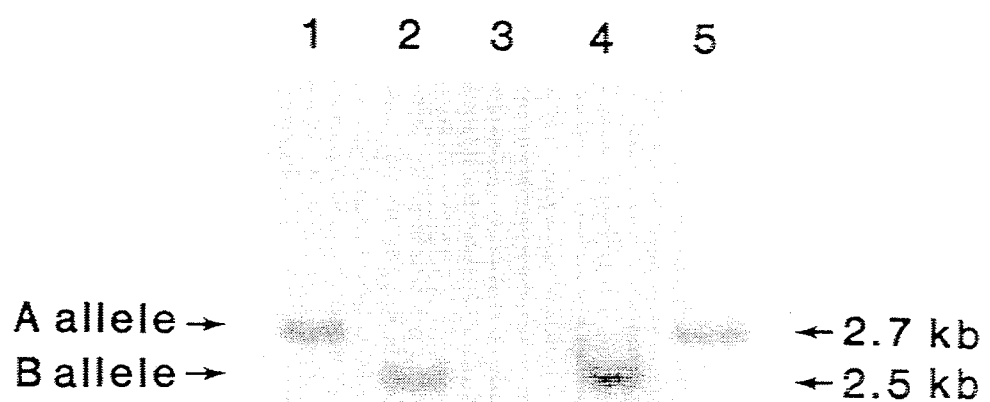
FIG. 1: Southern blot of genomic DNA and the genomic clone restricted with Hind III and probed with the 2.68 kb Hind III fragment. Lanes 1 to 4 represent genomic DNA (5 µg) from a keratinocyte cell line (A allele), HeLa (B allele), mouse spleen and somatic cell hybrid PGME 1 (7 µg) respectively, while lane 5 (0.008 ng) represents the Hind III 2.68 kb clone in pBluescript.

At its broadest, the invention comprises a method of detecting the presence of a DNA polymorphism associated with susceptibility to cancer in a human by analyzing human DNA or RNA using a hybridization probe or amplification primers containing nucleotide sequences complementary to the pseudogene of poly (ADP-ribose) polymerase. The probes and primers are chosen such that they are capable of identifying a restriction site polymorphism present within sequences of this pseudogene.

The use of restriction fragment length polymorphism (RFLP) is only one preferred embodiment of detecting polymorphism. Since, ultimately, the use of RFLP depends on polymorphism in DNA restriction sites along the nucleic acid molecule, other methods of detecting the polymorphism can also be used. Any method of analysis which allows one skilled in the art to determine the linkage between the polymorphism detected by the probes and primers of the present invention can be utilized. Techniques such as direct location of the polymorphism on chromosome 13 by in situ hybridization using radio labeled, fluorescent labeled, or enzyme labeled probes may be employed. Other suitable techniques include, but are not limited to, amplification methods such as the polymerase chain reaction, ribonuclease mis-match cleavage assay and direct oligonucleotide hybridization.

In one embodiment of the present invention, the preferred method involves RFLP techniques based on hybridization or sequence amplification. The following related definitions are provided to assure uniformity and to avoid ambiguity.

Poly (ADP-ribose)polymerase.

A chromatin associated enzyme which is a 113 kDa protein that uses NAD as a substrate to catalyze both the covalent transfer of ADP-ribose to a variety of nuclear protein acceptors and subsequently catalyzes the transfer of an additional 60-80 ADP-ribose units to the initial moiety.

Poly (ADP-ribose)polymerase pseudogene.

DNA sequences found on chromosome 13q33→qter which shows a high degree of homology to sequences encoding poly (ADP-ribose) polymerase.

Deoxyribonucleic Acid (DNA).

DNA is the molecular basis of heredity. DNA consists of a polysugar-phosphate backbone from which the purines and pyrimidines project. The backbone is formed by bonds between the phosphate molecule and carbon 3 and carbon 5 of adjacent deoxyribose molecules. The nitrogenous base extends from carbon 1 of each sugar. According to the Watson-Crick model, DNA forms a double helix that is held together by hydrogen bonds between specific pairs of bases (thymine to adenine and cytosine to guanine). Each strand in the double helix is complementary to its partner strand in terms of its base sequence.

Restriction Endonuclease.

A restriction endonuclease (also restriction enzyme) is an enzyme that has the capacity to recognize a specific base sequence (usually 4, 5, or 6 base pairs in length) in a double-stranded DNA molecule, and to cleave both strands of the DNA molecule at every place where this sequence appears. For example, Eco RI recognizes the base sequence GAATTC/CTTAAG.

Restriction Fragment.

The DNA molecules produced by digestion with a restriction endonuclease are referred to as restriction fragments. Any given genome will be digested by a particular restriction endonuclease into a discrete set of restriction fragments.

Restriction Fragment Length Polymorphism (RFLP).

The genomic DNA of two individuals in a population will differ in sequence at many sites either as a result of change in bases or insertions or deletions of sequences. When these differences occur in the recognition site for a restriction endonuclease, then a polymorphism in the length of restriction fragments produced by digestion of the DNA of the two individuals will result. For example, the hypothetical pattern of restriction fragments produced by digestion of A and B with restriction enzyme Eco RI exhibits a polymorphism, since the DNA of individual A yields two fragments f and g of lengths 2.6 kilobase pairs and 2.3 kilobase pairs, while DNA of individual B does not yield Eco RI fragments of this size after digestion with Eco RI, but instead gives a single fragment of length 4.0 kilobase pairs. As used herein, a polymorphism is also referred to as a "pattern."

Agarose Gel Electrophoresis.

To detect a polymorphism in the length of restriction fragments, an analytical method for fractioning double-stranded DNA molecules on the basis of size is required. The most commonly used technique (though not the only one) for achieving such a fractionalion is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by Eco RI. In order to visualize a small subset of these fragments, a methodology referred to as the Southern hybridization procedure can be applied.

Southern Transfer Procedure.

The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose is to draw the DNA from the gel into the nitrocellulose paper by capillary action.

Nucleic Acid Hybridization.

Nucleic acid hybridization is a technique which has been used in a wide variety of contexts in molecular biology since the basic principles governing reassociation of complementary nucleic acid molecules were discovered during the 1960s. Nucleic acid hybridization depends on the principle that two single-stranded nucleic acid molecules that have complementary base sequences will reform the thermodynamically favored double-stranded structure if they are mixed in solution under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe.

Hybridization Probe.

To visualize a particular DNA sequence in the Southern hybridization procedure, a labelled DNA molecule or hybridization probe is reacted to the fractionated DNA bound to the nitrocellulose filter. The areas on the filter that carry DNA sequences complementary to the labelled DNA probe become labelled themselves as a consequence of the reannealing reaction. The areas of the filter that exhibit such labelling are visualized. The hybridization probe is generally produced by molecular cloning of a specific DNA sequence from the human genome.

Sequence Amplification.

A method for generating large amounts of a target sequence. In general, one or more amplification primers are annealed to a nucleic acid sequence. Using appropriate enzymes, sequences found adjacent to, or in between the primers are amplified.

Amplification Primer.

An oligonucleotide which is capable of annealing adjacent to a target sequence and serving as an initiation point for DNA replication.

In one aspect of the methods of the present invention, a biological sample containing nucleated cells is obtained from a human. The nucleated cells are then isolated from the sample and the DNA from the nucleated cells is purified using means known in the art.

The isolated DNA is then digested with a restriction enzyme. Such enzymes include, but are not limited to, Hind III, Pst I, or Eco RI. The DNA fragments are then separated according to their molecular weights to form a pattern, typically using electrophoresis. The DNA polymorphism associated with a predisposition for cancer, if present, can be detected using a hybridization probe which will hybridize to the human poly (ADP-ribose) polymerase pseudogene.

Each restriction enzyme presents its own restriction fragment length pattern or polymorphism. In those humans with a predisposition for cancer, DNA digests with Hind III show two patterns: an "ab" pattern ($2.7 \pm 0.1$ kb and $2.8 \pm 0.2$ kb) and a "b" pattern ($2.5 \pm 0.1$ kb). Normal humans show a Hind III restriction fragment pattern of about $2.8 \pm 0.1$ kb. See FIG. 1

DNA digests with Psi I show a polymorphism of about 5.7 to about 6.1 kilobases in those humans with predispositions for cancer. Normal humans show a restriction fragment of about 7 to about 7.5 kilobases in Pst I digests.

DNA digests with Eco RI show a polymorphism of about 5.1 in those humans with a predisposition for cancer. Normal humans show a restriction fragment of about 5.3 in Eco RI digests.

As used herein, the term "normal" means those individuals that do not display any cancerous or precancerous conditions, measured by clinical, symptomatic or morphological means.

In another embodiment of the present invention, the progression of a tumor's pathogenicity in tumor biopsy samples can be followed. By examining the changes in the polymorphic bands in patients with cancer, this method can be used for monitoring tumor therapy in diseases such as metasiatic cancer, solid tumors, and AID's related lymphomas. Thus, the probe can be used in the method of the present invention to establish the polymorphisms in the tumor sample. After treatment for cancer, by chemotherapy or radiotherapy, the biopsy tumor sample can again be assayed for the presence of the polymorphisms. Using the Hind III restriction enzyme, for example, it has been determined that in cancer patients who have an ab pattern before treatment (with bands showing at 2.7 and 2.9 kb), there is a loss of the 2.9 kb (a) band after treatment, with a concomitant reduction in the pathogenicity of the tumor.

The size of the DNA fragments are given in ranges because it is well known that due to the nature of the techniques used in determining fragment size, small differences in measurements results are not uncommon. These differences do not, however, detract from the accuracy of the numbers given.

As used herein, the term "humans with a predisposition or with a susceptibility for cancer" is meant to include individuals that may not yet show or display any cancerous or precancerous conditions, as measured by symptomatic means, but may be inclined to develop cancer. As detailed in the data in the Examples, all cancer patients tested showed the polymorphisms or patterns when tested according to the method of this invention, individuals that did not have cancer or precancerous conditions did not show these polymorphisms or patterns. A small group of individuals that did not have cancer or precancerous conditions did show the polymorphisms or patterns. These individuals, or others who also show these patterns, need to be followed to determine if individuals subsequently show precancerous or cancer cells.

The types of cancers for which a predisposition may be detected by the methods of the invention include, but are not limited to, Burkitt's lymphoma, B follicular cell lymphoma, small cell lung carcinoma, colon-rectal carcinoma and breast adenocarcinoma.

Suitable biological samples having nucleated cells that may be used in this invention include, but are not limited to, blood, semen and tissue. The method of obtaining the biological sample will vary depending upon the nature of the sample.

By the term "nucleated cells" is meant any cell containing a nucleus. Examples of such cells include, but are not limited to, white blood cells, epithelial cells, sperm cells, or mesenchymal cells. Such cells may either be normal or neoplastic.

DNA from the nucleated cells is isolated, using any of the techniques known to those skilled in the art of the invention. For instance, DNA can be isolated using various lytic enzymes or chemical solutions and centrifugation (Blin et al., *Nucl. Acid Res.* 3:2303–2308 (1976)). DNA may also be isolated using size exclusion chromatography.

After the DNA is isolated from the cells' nuclei, it is digested with a given restriction endonuclease. The restriction endonucleases that may be used in this invention include, but are not limited to Hind III, Pst I, or Eco RI.

Given the ability of the probes of the present invention to detect polymorphism on Chromosome 13q33→qter, it is possible that other RFLPs may be detected using other restriction enzymes. For example, these restriction enzymes may include, but are not limited to Msp I, Not I and Cla I.

After a digest is obtained, and the DNA is separated by standard technique, for example by agarose gel electrophoresis, the separated bands are probed with a DNA fragment encoding poly (ADP-ribose) polymerase. In one embodiment, the preferred probe of the invention is based on the cDNA sequence encoding human poly (ADP-ribose)polymerase. Alternatively, a probe based on the pseudogene sequence disclosed herein may also be used as the probe.

Any size fragment of the poly (ADP-ribose) polymerase cDNA or pseudogene can be utilized as a probe as long as it is capable of hybridizing to a restriction fragment which displays a polymorphism within chromosome 13q33→qter. Further, any probe may be used which detects sequences linked or associated with the pseudogene on chromosome 13. The cDNA sequence of the preferred probe has been described in Cherney et al. *PNAS(USA)*, 84:8370–8374 (1987), herein incorporated by reference. In addition, the probe may hybridize to a portion or fragment of the gene for poly (ADP-ribose) polymerase or genes or sequences linked or associated with poly (ADP-ribose) polymerase.

Alternatively, the probe utilized in the present method can be based on the DNA sequence of the poly (ADP-ribose) polymerase pseudogene located on chromosome 13 (Seq. ID. Nos. 3 or 4, A and B alleles, respectively). A probe based on the pseudogene sequence can be allele specific, hybridizing only to either the A or B allele, or can hybridize to both alleles so long as it detects a restriction site polymorphism. One skilled in the art can readily design such probes based on the sequence disclosed herein using methods of computer alignment and sequence analysis known in the art.

In another embodiment, more than one restriction enzyme is utilized for the detection of the polymorphism associated with a predisposition for cancer. Thus, DNA from the biological sample can be subjected to three separate restriction enzyme digests using Hind III, Pst I, and Eco RI. It is to be understood that three digests are conducted on three separate DNA samples, the samples being obtained from the same biological source.

The hybridization probes of the present invention can be labelled by standard labelling techniques such as with a radiolabel, enzyme label, fluorescent label, biotin-avidin label, chemiluminescence, and the like. After hybridization, the probes are visualized using known methods. Comparison of the RFLP or RFLP's for the subject under investigation will quickly reveal the presence or absence of the polymorphism linked to predisposition to cancer.

In a further embodiment, methods including amplification of the target sequence prior to detection, such as PCR, are utilized to identify which allele is present in a sample (Innis et al., *PCR Protocols*, Academic Press New York (1990)). Specifically, utilizing the sequences disclosed for the processed pseudogene, allele specific amplification primers can be designed for differentiating between the α and β alleles of the processed pseudogene.

In one aspect of this embodiment, the sequence of the primers are based on the sequence of the pseudogene (Seq. ID. Nos. 3 and 4) which flank a region which differs in size between the two alleles. In such an embodiment, the two alleles will yield fragments of different size after amplification. Such size difference can be visualized using standard electrophoretic procedures. In this aspect, primers whose sequences are 5'-AAGAAGCCAACATCTGAGCT-3' (Seq. ID. No 1) and 5'-TTTCCTTGTCATCCTTCAGC-3' (Seq. ID. No 2) are preferred.

Alternatively, sequences flanking a restriction site polymorphism can be utilized as primers. In such an embodiment the amplified product is subjected to restriction digestion prior to visualization. In such an embodiment, the two alleles will yield amplified fragments of differing size after digestion with an appropriate restriction endonuclease.

The materials for use in the invention are ideally suited for the preparation of a kit. Specifically, the invention provides a compartmentalized kit to receive in close confinement, one or more containers which comprises: (a) a first container comprising one of the or more of the probes or amplification primers of the present invention; and (b) one or more other containers comprising one or more of the following: a sample reservoir, wash reagents, reagents capable of detecting presence of bound probe from the first container, or reagents capable of amplifying sequences hybridizing to the amplification primers.

In detail, a compartmentalized kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (Tris-buffers, etc.), and containers which contain the reagents used to detect the bound probe or amplified product.

Types of detection reagents include labelled secondary probes, or in the alternative, if the primary probe is labelled, the enzymatic, or antibody binding reagents which are capable of reacting with the labelled probe. One skilled in the art will readily recognize that the disclosed probes and amplification primers of the present invention can readily be incorporated into one of the established kit formats which are well known in the art. In one example, a first container may contain a hybridization probe. The second container may contain the restriction enzyme to be used in the digest. Other containers may contain reagents useful in the localization of labelled probes, such as enzyme substrates such as x-gal tagged avidin if a biotinylated probe is utilized. Still other containers may contain buffers, etc.

The present invention is further based on the observation that the pseudogene described herein contains an open reading frame which is capable of being translated into a peptide whose amino acid sequence is depicted in Seq. ID No. 6 (hereinafter the pseudo-gene peptide). Thus, the present invention is further directed to the pseudogene peptide, substantially free of natural contaminants.

Any eukaryotic organism can be used as a source organism for the pseudogene peptide, or the genes encoding same, as long as the source organism naturally contains such a peptide or can be transformed so as to express the pseudogene peptide. As used herein, "source organism" refers to the original organism from which the amino acid or DNA sequence of the pseudogene peptide is derived, regardless of the organism the subunit is expressed in and ultimately isolated from. For example, a pseudogene peptide expressed in insect cells is of human origin as long as the amino acid sequence is that of Seq. ID No. 6. The most preferred source organism is human.

A variety of methodologies known in the art can be utilized to obtain the pseudogene peptide of the present invention or the gene encoding same. In one embodiment, the peptide is purified from tissues or cells which naturally produce the peptide. One skilled in the art can readily follow known methods for isolating proteins in order to obtain the peptide free of natural contaminants. These include, but are not limited to, immunochromotography, HPLC, size-exclusion chromatography, ion-exchange chromatography, and immunoaffinity chromatography.

In another embodiment, the pseudogene peptide is purified from cells which have been altered to express the pseudogene peptide As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells in order to generate a cell which produces the pseudogene peptide.

There are a variety sources for DNA encoding the pseudogene peptide. The DNA can be isolated as described herein from a source such as human, or, alternatively, the sequence encoding the pseudogene peptide can be synthesized utilizing the DNA sequences disclosed herein.

Any host/vector system can be used to express the pseudogene peptide. These include, but are not limited to, eukaryotic hosts such as Hela cells, Cv-1 cell, COS cells, and Sf9 cells, as well as prokaryotic host such as *E. coli* and *B. subtilis*. The most preferred cells are those which do not normally express the pseudogene peptide or which express it at low levels.

The pseudogene peptide of the present invention can be used in a variety procedures and methods.

In one embodiment, the pseudogene peptide is used to generate an antibody which is capable of binding to the peptide (anti-pseudogene peptide antibodies).

The anti-pseudogene peptide antibodies of the present invention include monoclonal and polyclonal antibodies, as well fragments of these antibodies, and humanized forms of the monoclonal antibodies. Humanized forms of the antibodies of the present invention may be generated using one of the procedures known in the art such as chimerization or CDR grafting.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (Campbell, A. M., "*Monoclonal Antibody Technology: Laboratory Techniques in Biochemistry and Molecular Biology,*" Elsevier Science Publishers, Amsterdam, The Netherlands (1984); St. Groth et al., *J. Immunol. Methods* 35:1-21 (1980)).

Any animal (mouse, rabbit, etc.) which is known to produce antibodies can be immunized with the pseudogene polypeptide. Methods for immunization are well known in the art. Such methods include subcutaneous or interperitoneal injection of the polypeptide. One skilled in the art will recognize that the amount of pseudogene peptide used for immunization will vary based on the animal which is immunized, the antigenicity of the peptide and the site of injection.

The pseudogene peptide may be modified or administered in an adjuvant in order to increase the peptide antigenicity. Methods of increasing the antigenicity of a polypeptide are well known in the art. Such procedures include coupling the antigen with a heterologous protein (such as globulin or $\beta$-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109-124 (1988)).

Hybridomas secreting the desired antibodies are cloned and the class and subclass is determined using procedures known in the art (Campbell, A. M., *Monoclonal Antibody Technology: Laboratory Techniques in Biochemistry and Molecular Biology,* Elsevier Science Publishers, Amsterdam, The Netherlands (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labelled. Antibodies can be detectably labelled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labelling are well-known in the art, for example see (Sternberger, L. A. et al., *J. Histochem. Cytochem.* 18:315 (1970); Bayer, E. A. et al., *Meth. Enzym.* 62:308 (1979); Engval, E. et al., *Immunol.* 109:129 (1972); Goding, J. W. *J. Immunol. Meth.* 13:215 (1976)). The labeled antibodies of the present invention can be used for in vitro, in vivo, and in situ assays to identify cells or tissues which express the pseudogene peptide or identify samples containing the pseudogene peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., "

Handbook of Experimental Immunology" 4th Ed., Blackwell Scientific Publications, Oxford, England, Chapter 10 (1986); Jacoby, W. D. et al., *Meth. Enzym.* 34 Academic Press, New York (1974)). The immobilized antibodies of the present invention can be used for in vitro, in vivo, and in situ assays as well as for immunoaffinity purification of the pseudogene peptide.

In another embodiment, the anti-pseudogene peptide antibodies are used to generate anti-idiotypic antibodies.

Anti-idiotypic antibodies can be generated by any of the methods described above using one of the antibodies of the present invention as an immunogen. One skilled in the art can readily adapt known methods in order to generate the anti-idiotypic antibodies capable of binding to the antigen binding site of the anti-pseudogene peptide antibodies of the present invention.

In another embodiment of the present invention, methods of identify the expression of the pseudogene peptide in a test sample are presented.

In detail, the methods comprise incubating a test sample with one or more of the antibodies of the present invention and assaying whether the antibody binds to the test sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, T. "*An Introduction to Radioimmunoassay and Related Techniques*" Elsevier Science Publishers, Amsterdam, The Netherlands (1986); Bullock, G. R. et al., "*Techniques in Immunocytochemist,*" Academic Press, Orlando, Fla. Vol. 1 (1982), Vol. 2 (1983), Vol. 3 (1985); Tijssen, P., "*Practice and Theory of Enzyme Immunoassays: Laboratory Techniques in Biochemistry and Molecular Biology,*" Elsevier Science Publishers, Amsterdam, The Netherlands (1985).

The test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

In another embodiment of the present invention, kits are provided which contain the necessary reagents to carry out the previously described assays.

Specifically, the invention provides a compartmentalized kit to receive, in close confinement, one or more containers which comprises: (a) a first container comprising one of the antibodies of the present invention; and (b) one or more other containers comprising one or more of the following: wash reagents, reagents capable of detecting presence of bound antibodies.

In detail, a compartmentalized kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody.

Types of detection reagents include labelled secondary antibodies, or in the alternative, if the primary antibody is labelled, the enzymatic, or antibody binding reagents which are capable of reacting with the labelled antibody. One skilled in the art will readily recognize that the disclosed antibodies of the present invention can readily be incorporated into one of the established kit formats which are well known in the art.

In another embodiment of the present invention, methods are provided for identifying agents which are capable of binding to the pseudogene peptide of the present invention.

In detail, said method comprises:
 (a) contacting a compound with purified pseudogene peptide; and
 (b) determining whether the agent binds to the peptide.

The agents screen in the above assay can be, but is not limited to, peptides, carbohydrates, or vitamin derivatives. The agents can be selected and screened at random or rationally selected or designed using protein modeling techniques.

For random screening, agents such as peptides, or carbohydrates are selected at random and are assayed for there ability to bind to the pseudogene peptide.

Alternatively, agents may be rationally selected or designed. As used herein, an agent is said to be "rationally selected or designed" when the agent is chosen based on the configuration of the pseudogene peptide. For example, one skilled in the art can readily adapt currently available procedures to generate peptides capable of binding to a specific peptide sequence in order to generate rationally designed antipeptide peptides, for example see Hurby et al., Application of Synthetic Peptides: Antisense Peptides", In *Synthetic Peptides, A User's Guide,* W. H. Freeman, New York, pp. 289–307 (1992), and Kaspczak et al., *Biochemistry* 28:9230-8 (1989).

In another embodiment of the present invention, methods for decreasing the activity of the pseudogene peptide can be modulated by providing an agent capable of binding to the peptide. Such agents include, but are not limited to, the anti-pseudogene peptide antibodies and the antipeptide peptides of the present invention. By decreasing the activity of the pseudogene peptide, the effects which the expression of the peptide has on tumor formation and tumor development can be decreased.

In another embodiment of the present invention, methods are presented for decreasing the expression of the pseudogene disclosed herein. Specifically, anti-sense RNA expression is used to disrupt the translation of the pseudogene message.

In detail, a cell is modified using routine procedures such that if expresses an antisense message, a message which is complementary to the pseudogene message. By constitutively or inducibly expressing the antisense RNA, the translation of pseudogene mRNA can be regulated. Such antisense technology has been successfully applied to regulate the expression of poly(ADP-ribose) polymerase (Ding et al., *J. Biol. Chem.* 267: 12804–12812 (1992)).

Having now generally described the invention, the same will be understood by means of specific examples which are, however, not intended to be limiting unless otherwise specified.

EXAMPLE 1

Burkitt's lymphoma is a neoplasm of B lymphocytes. Two subtypes of this disease have been described, endemic and sporadic, which differ at clinical and biological levels. Klein, *Cellular Oncogene Activation,* Marcel Dekker, Inc. (1988). Both forms are associated with consistent chromosomal translocations that place the c-myc proto-oncogene, a gene associated with cell proliferation, within or in proximity to an immunoglobulin chain gene locus.

The mouse plasmacytoma system offers the closest analogy to the human Burkitt's tumor. Thus, mouse plasmacytomas (MOPC) are B cell neoplasms, and like Burkitt's lymphoma, are closely associated with a translocation that places the myc proto-oncogene under the putative control of an immunoglobulin locus. Furthermore, it has been suggested that the anatomical involvement of the jaw in endemic Burkitt's may be related to a prerequisite inflammatory condition, similar to the obligate requirement of pristine in induction of plasmacytomas in susceptible strains.

Observations from MOPC studies prompted studies to determine whether structural differences in the polymerase gene(s) would be present in the human analog of the MOPC system. Initially, the possible genotypes for the polymerase gene(s) from human DNA were defined. When human genomic DNA from several sources was digested with Hind III, three main patterns were distinguishable:

(1) a single band present at 2.8 kb (genotype ab);
(2) two bands present in that region at 2.8 and 2.6 kb (haploid ab); or
(3) a single band present at 2.6 kb (genotype b).

Based on hamster and human somatic cell hybrids, it had been previously shown that these bands arise from chromosome 13. When the same DNA samples were analyzed after digesting them with Pst I, a band of 5.6 kb in all samples that had an ab genotype. In samples with a "b" genotype it could be deduced that this band arose from a 7 kb Pst I band. This suggested that the polymorphism in the Hind III 2.8 kb band probably arose as a result of deletion involving a Pst I site flanking the polymerase gene on chromosome 13.

Figure 3:
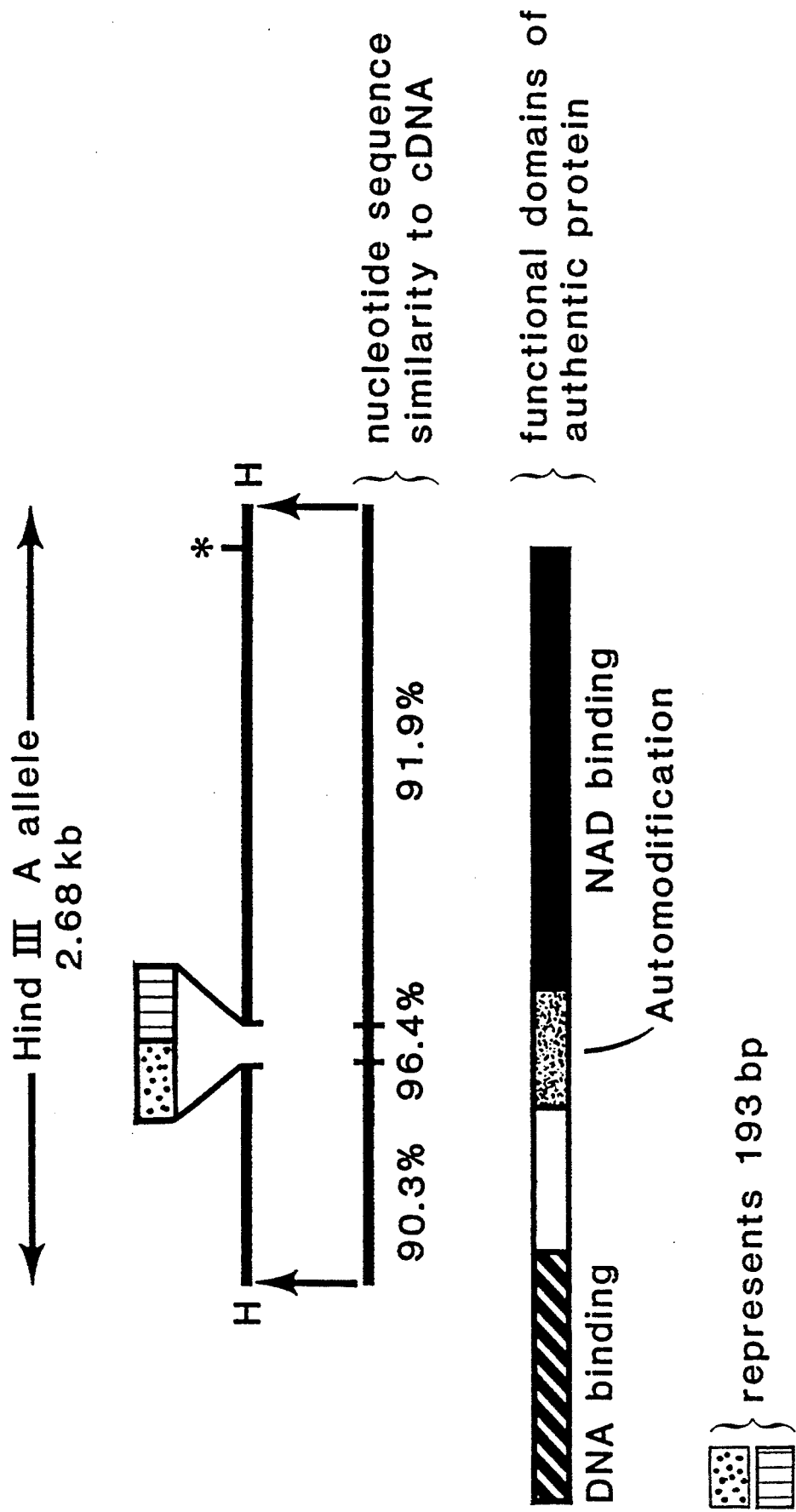
FIG. 3: A schematic representation of the relationship of the isolated Hind IIIA allele to the functional domains of the authentic PADPRP protein.

To confirm this finding, the same genomic DNA was digested with Eco RI. Since it had been earlier shown that the 5.3 kb band in the Southern digests of total genomic DNA represents polymerase sequences on chromosome 13, a deletion event in this region to yield a lower hybridizing band was expected. As is seen in FIG. 3, it was found that DNA samples representing genotypes ab or b resulted in an Eco RI band of slightly greater mobility than the 5.3 kb band in genotype a, typically a 5.1 kb band.

To further analyze the frequency of these genotypes in a control population, DNA from 94 non-cancer individuals was screened. As described in Table I, genotype a was found to be the most predominant form in this sample population. Thirteen of the 94 individuals showed an ab genotype. In the total normal cell population screened, no individuals with a b genotype could be found. Since both the 2.7 kb and the 2.6 kb Hind III bands are allelomorphic, one would expect, based on Mendelian inheritance, to find a subpopulation for the b genotype. Thus, it is thought that based on the Hardy Weinberg principle, the b genotype would be of a low frequency.

EXAMPLE 2

Human Studies of DNA from Burkitt's Lymphoma.

DNA from 45 Burkitt's lymphoma was also studied. These included both cell lines and primary tumor samples. This sample size was comprised of 20 samples from endemic Burkitt's lymphomas and 23 from sporadic Burkitt's lymphomas. The samples were digested with Hind III.

The results showed that the total frequency of an ab or b genotype in these samples was significantly greater than in control samples. Thus approximately 70% of total Burkilt's lymphoma DNA was polymorphic for the rarer genotypes. In endemic Burkitt's, the frequency of this pattern approached 100% (19/20), a high proportion of which were of b genotypes (42%) 19/20. In sporadic Burkitt's the frequency of ab or a "b" genotype was significantly greater than in normal, non-cancer individuals (11 out of 23 cases compared to 14 out of 94 normal cases).

In sporadic Burkilt's, we also found that the presence of ab or b genotype cosegregated with the EBV status. Thus, almost 100% of the polymorphic samples from sporadic Burkitt's were EBV negative (−). In fact, the only EBV + sample was from a patient who was a native of Africa, but developed BL several years after living in the USA. Since almost all samples from endemic Burkitt's showed genotype b or ab and since endemic Burkitt's is almost always associated with EBV, the presence of this genotype appears to reflect an independent factor involved with the induction of Burkitt's lymphoma. The results on these studies are summarized in Table II.

The presence of increased frequency of an altered polymerase gene in Burkitt's lymphoma corroborates the observations of K. Sanford that certain Burkilt's cell lines are deficient in DNA repair following X-irradiation, similar to the observations with cells from the plasmacytoma susceptible and resistant mouse strains (Gantt et al., *Radiat. Res.* 108:117–126 (1986)). A constraint to the key involvement of the polymerase and DNA repair deficiency in both Burkitt's and plasmacytoma formation is the selectivity of the transformed target cell. Thus, in contrast to other DNA deficient conditions, for example Fanconi's anemia and Blooms syndrome that predispose towards development of a wide variety of tumors, one would have to hypothesize a selective mode of polymerase involvement in B cells.

EXAMPLE 3

Human Studies on Hematological Malignancies.

It has recently been suggested that a number of hematological malignancies could arise as a result of aberrant recombination mediated by the immunoglobulin recombinase. A common factor for such malignancies is the juxtaposition of a proto-oncogene to an Ig loci. It is possible that the polymerase plays a role in immunoglobulin recombinase systems and the isotype switching. Aberrant recombination events would be increased in frequency in presence of a defective polymerase gene and such individual, would be predisposed to the development of B cell neoplasia that results from translocations at the Ig loci.

To test this hypothesis DNA samples from B Follicular cell lymphomas, Acute/Chronic Myeloid leukemias ("AML/CML") and Small cell lung carcinomas ("SCLC") were analyzed using Hind III. Since B follicular lymphomas are associated with a translocation of a proto-oncogene in the Ig loci, we would expect to find increased frequency of ab or b genotypes in these samples. Conversely since AML/CML and SCLC's are non lymphoid tumors, we would expect a normal distribution of the genotypes.

An increased frequency of ab and b genotypes was found in samples from B follicoular lymphomas. Of 24 samples, 11 of 19 samples were found to show a translocation to have either an ab or a b genotype. 10 samples of myeloid tumors were examined and no increase in the frequency of ab or b genotype distribution in these samples was found. However, in SCLC samples we again found a very high frequency of ab or b genotypes. This sample population the presence of ab or b genotype cosegregated with the presence of amplified L-myc Prins et al., Anticancer Res. 13:1373–1386 (1993), so that 100% of the Lmyc amplified cases had either an ab or a "b" genotype. We also found three out of four non-small cell lung tumors to be polymorphic as shown in Table IV It thus appeared that the increased frequency of the ab or b genotype did not correlate selectively with lymphoid malignancies. Since these genotype patterns are localized to chromosome 13 and it has been suggested that the sequences on chromosome 13 may represent a pseudogene, it is possible that the deletion event on chromosome 13 as observed by using the polymerase cDNA is not functionally related to the polymerase, but that the polymerase sequences have provided a fortuitous linkage marker for a possible recessive gene involved in predisposition to certain types of tumors.

Indeed, when the different cell types (those with "a", "ab" or "b" genotype were examined) for changes in the enzymatic activity and or the protein content of the polymerase, no correlation with altered gene structure and enzymatic activity was found as observed both by activity gel analysis and NAD content of the cells or by immunoquantitation. A number of Burkitt's cell lines that represented all the three genotypes in the sample population were analyzed by Northern analysis. The results did not indicate any obvious differences in transcripts for the polymerase in these cells.

Recently Harbour described abnormalities in the structure and expression of another gene on chromosome 13, the Retinoblastoma gene, in various SCLC cell lines (Science 241:353–357 (1988)). These findings were compared to deletion events on chromosome 13 linked to the polymerase. As seen in Table V, there is a strong association of the polymerase linkage marker in the various samples we analyzed.

Since there is evidence in certain tumors that the inactivation of both alleles of certain genes triggers tumorigenesis and since no single normal DNA sample with a b genotype has been observed, but in contrast frequently a "b" genotype in tumor DNA has been found, it has been concluded that such a genotype could arise in certain cases by a deletion event affecting an "ab" genotype. To test this hypothesis, matched tumor and lymphocyte DNA samples for genotype characterization were analyzed. In all samples with b genotypes, it was found that the corresponding lymphocyte DNA has an ab genotype. Thus, it is possible that the b genotypes observed in earlier tumor samples could have arisen by a similar mechanism.

In all our samples from the tumor tissues, 19 samples with a "b" genotype have been found. In an equal control sample size no "b" genotype was found.

EXAMPLE 4

Human Studies on Breast Adenocarcinoma.

Since it has been suggested that breast adenocarcinoma is associated both with a heritable factor and a putative recessive oncogene, screening was extended to breast adenocarcinomas. As seen in Table VI, 23 of 55 samples were found to be polymorphic. Among the samples that were matched for tumor and lymphocyte DNA, of significant interest were four samples, a sample that showed a conversion of the a genotype to an ab genotype in the tumor cells, two others that showed a conversion of an ab genotype to a "b" genotype in the tumor cells. In one case, the tumor genotype was found to be a but the somatic genotype to be ab. However, in this case there appeared to be an amplification event suggesting that the a genotype in the tumor probably arose of a chromosomal rearrangement, thus, further supporting the earlier observation that the b genotype is tumor specific.

The linkage of Rb and poly(ADP-Ribose) polymerase has now been characterized on chromosome 13 and it is known that the polymerase is localized further down from the R6 on 13q. It is situated close to the ter. In accordance with Knudson's ingenious hypothesis (Natl. Cancer Inst. Monogr. 51:19–24 (1979)), it is proposed that this deletion event on chromosome 13 as observed by the cDNA to the poly(ADPR-Ribose) polymerase, represents a part of the two hit event, both heritable and somatic. Taken together, these findings strongly suggest the involvement of a recessive oncogene linked closely to the polymerase gene on chromosome 13 and independent of Rb in the pathogenesis of several malignancies. Since this deletion on chromosome 13 affects a number of tumor types, it has been proposed to call this region M.E.S., for multiple etiological suppressor.

TABLE I

| SUMMARY OF RFLP ANALYSIS IN NORMAL POPULATION | |
|---|---|
| Total Cases | 94 |
| 'A' Genotype | 80 |
| AB Genotype | 14 |
| B Genotype | 0 |

TABLE II

SUMMARY OF PADPR RFLP ANALYSIS IN BURKITT'S LYMPHOMA

| | Polymorphic | | |
|---|---|---|---|
| | 'B' Genotype | 'AB' Genotype | Normal |
| Sporadic EBV + | 1 | 0 | 7 |
| EBV − | 1 | 9 | 5 |
| Endemic | 8 | 11 | 1 |
| Not Known | 0 | 1 | 1 |
| TOTAL CASES | | 45 | |
| AB GENOTYPES | | 20 | |
| B GENOTYPES | | 10 | |

TABLE III

RFLP ANALYSIS IN B FOLLICULAR LYMPHOMAS

| | Polymorphic | | |
|---|---|---|---|
| | 'B' Genotype | 'AB' Genotype | Normal |
| Translocations | 4 | 7 | 8 |
| No Translocation | 0 | 0 | 4 |
| Non-Follicular | 0 | 0 | 1 |
| TOTAL CASES | | 24 | |
| AB GENOTYPES | | 7 | |

TABLE III-continued
RFLP ANALYSIS IN B FOLLICULAR LYMPHOMAS

|  | Polymorphic | | |
|---|---|---|---|
|  | 'B' Genotype | 'AB' Genotype | Normal |
| B GENOTYPES |  | 4 |  |

TABLE IV
LUNG TUMORS

|  | Polymorphic | | |
|---|---|---|---|
|  | 'B' Haplotype | 'AB' Haplotype | Normal |
| SCLC |  |  |  |
| LMYC Amplification | 2 | 4 | 0 |
| N/C MYC Amplification | 1 | 0 | 5 |
| No Amplification | 0 | 3 | 5 |
| NON SCLC | 1 | 2 | 1 |
| TOTAL CASES |  | 24 |  |
| AB HAPLOTYPES |  | 9 |  |
| B HAPLOTYPES |  | 4 |  |

TABLE V
LUNG CANCER LINES

| Tumor | Cell Line | myc activation | Chromosome RB | 13 markers ADPRT |
|---|---|---|---|---|
| 1. SCL | 207 | L-myc | − | + |
| 2. SCLC | 187 | N-myc | + | − |
| 3. SCLC | 82 | c-myc | − | − |
| 4. SCLC | 417 | c-myc | − | − |
| 5. SCLC | 128 | L-myc | − | + |
| 6. SCLC | 69 |  | − | − |
| 7. SCLC | 378 | L-myc | + | + |
| 8. SCLC | 510 | L-myc | − | + |
| 9. SCLC | 345 | L-myc | + | + |
| 10. SCLC | 592 | N-myc | − | − |
| 11. non-SCLC | 787 |  | ND | + |
| 12. non-SCLC | 788 |  | ND | + |
| 13. non-SCLC | 789 |  | ND | + |
| 14. non-SCLC | 790 |  | ND | − |

SCLC = Small Cell Lung Carcinoma
+ = DNA somatic alteration
ND = not determined

TABLE VI
RFLP ANALYSIS IN BREAST TUMORS

| Polymorphic |  |
|---|---|
| A Genotype | 19 |
| B Genotype | 2 |
| Normal | 32 |
| TOTAL | 55 |

EXAMPLE 5
Isolation of a chromosome 13 PADPRP genomic clone

A recombinant DNA library containing Hind III inserts prepared from flow sorted chromosome 13 and the phage vector Charon 21A was screened using full-length PADPRP cDNA. This library has successfully been used to isolate DNA markers for the 13q14 region (Lalande et al., *Cancer Genet. Cytogenet.* 13:283–295 (1984)). Approximately 50,000 phage were screened under stringent hybridization and wash conditions.

DNA was isolated from the positive genomic clones, digested with Hind III and subcloned into dephosphorylated, Hind III digested pBluescript (Stratagene) by standard techniques (Sambrook et al., *Molecular Cloning: A Laboratory Manual*, New York, Cold Spring Harbor Laboratory (1989)). The DNA was sequenced by the dideoxynucleotide chain-terminating method (Sanger et al., *Proc. Natl. Acad. Sci. USA* 74:5463–5467 (1977)) using Sequenase (U.S. Biochemical). Initially, the 5' and 3' termini of the clones were determined using primers to the T3 and T7 promoter regions. The entire sequence was determined on both strands by multiple rounds of sequencing using a series of oligonucleotides obtained from the sequential reaction. The products of the polymerase chain reaction (PCR) were gel isolated, and sequenced on both strands from independent reactions using primers generated from the sequence in FIG. 2.

Sequence data were analyzed using the Genetic Computer Group (GCG) program (Madison, Wis.). Southern blotting, hybridization conditions and preparation of peripheral blood lymphocytes were performed as previously described (Bhatia et al., *Cancer Res.* 50:5406–5413 (1990)). Germline DNA was obtained from peripheral blood lymphocytes.

EXAMPLE 6
Frequency of the PADPRP B allele genotype in germline derived DNA from black cancer patients An important aspect of the earlier study (Bhatia et al., *Cancer Res.* 50:5406–5413 (1990)) was the observation that one copy of the B allele was always present in tumor tissue from patients with endemic Burkitts lymphoma, and the frequency of the B allele was at least two-fold higher than in the black, noncancer population. Since there was no loss of heterozygosity in 95% of the matched samples analyzed, normal DNA from peripheral blood lymphocytes was used to screen patients for the PADPRP polymorphism. In the initial study, a limited survey of germline DNA derived from black patients having various cancers showed a 1.7-fold increase in the B allele frequency which compared favorably with the data collected for endemic Burkitts lymphoma (Bhatia et al., *Cancer Res.* 50:5406–5413 (1990)). Thus, we extended the analysis to include specific cancers (multiple myeloma, prostate and lung cancer) which occur more frequently among US blacks than whites. It has been suggested that racial differences in the cancer incidence rates are mainly attributed to socioeconomic factors. However, it is not well understood whether a genetic basis contributes to the observed epidemiological data. We have used the polymorphic PADPRP DNA marker on chromosome 13 associated with a predisposition to certain cancers, to gain insights into understanding how a genetic basis may account for a high occurrence of specific cancers in the black population.

To determine whether the high frequency of the B allele observed in patients with endemic Burkitts lymphoma was also found in another B cell malignancy, we analyzed germline DNA for the PADPRP genotype from 68 patients who had various stages of multiple myeloma using southern blotting of PCR amplification products. Multiple myeloma is the only hematopoietic malignancy for which the incidence in blacks is twice that observed among whites (Riedel et al., in: *Neoplastic Diseases of the Blood and Blood Forming Organs*, Wiernik et al., eds., New York: Churchill-Livingston, Inc., pp. 347–372 (1991)). It has been postulated that immunological determinants such as the human leukocyte antigens (HLA) may contribute to the racial difference in incidence rates (Pottern et al., *Can. Epid. Bio. & Prev.* 1:177–182 (1992)). Thus, analysis of the PADPRP polymorphism in patients with multiple myeloma may provide a non-immunological marker for determining a predisposition to this cancer among different racial populations.

Genomic DNA (100-400 ng) or plasmid DNA (1-2 ng) was amplified using the primers 5'-AAGAAGC-CAACATCTGAGCT-3' (Seq. ID No. 1) and 5'-TTTCCTTGTCATCCTTCAGC-3'(Seq. ID No. 2) for 30 cycles of the following: 45s at 94° C., 1 min at 62° C. and 2 min at 72° C. The reaction was carried out in 100 µl volume containing 2.5 units of AmpliTaq DNA Polymerase (Perkin Elmer Cetus), 10 mM Tris-HCl, pH 8.3, 50 mM KCl, 2.5 mM $MgCl_2$, 0.001% (w/v) gelatin and 0.2 mM of each deoxynucleoside triphosphate.

Of 31 black patients with multiple myeloma the frequency of the PADPRP B allele as 0.66, nearly double that observed in the noncancer population (Table VII). In contrast, the frequency of the B genotype among the white patients was no different from the appropriate control group.

Prostate cancer is another cancer of high occurrence among U.S. blacks and is at least 50% higher than in the white population (Gloeckler Ries et al., Cancer Statistics Review 1973-1987 (Bethesda, Md.: U.S. Dept. of Health and Human Services) (1990)). Since the incidence of prostate cancer is higher among blacks in the U.S. than in Africa, an interaction between genetic and environmental factors is clearly involved. However there is only a limited knowledge on the exact environmental factors which contribute to the etiology of this disease. The frequency of the B allele was 0.72 among the black patients, which was twice as high as that observed in the noncancer population (Table 7). On the other hand, none of the sixteen patients in this cohort of white patients showed the homozygous BB genotype, and the B allele frequency (0.19) did not differ from the control, noncancer group (0.14).

Notably for lung cancer, we observed a 1.7 and 2.4 times increase in the frequency of the B allele for black and white patients respectively, compared to the control group (Table 7). However, the increase in B allele frequency was not statistically significant (p>0.05), probably since these groups included an insufficient number of patients. Germline DNA from two other groups of black patients having either colon or breast cancer were also analyzed for the PADPRP genotype. Of ten black patients with colon cancers, no individual was homozygous for the A allele and the frequency of the B allele was elevated almost two-fold. In contrast, the homozygous A allele was dominant in an analysis of twenty-one black women with breast cancer, and in our experience this was one of the few cancers thus far studied which did not appear to be correlated with an increased frequency of the PADPRP B allele.

To summarize, for multiple myeloma, prostate and colon cancer an increased frequency of the B allele appeared to be striking in germline DNA from black patients. On the other hand, the distribution of the B genotype did not differ significantly among the white cancer patients compared to the noncancer population.

EXAMPLE 7

Analysis of the PADPRP sequences on chromosome 13

Previously, we used the full-length PADPRP cDNA to monitor the RFLP's associated with the PADPRP sequences on chromosome 13 Bhatia et al., Cancer Res. 50:5406-5413 (1990)). Hybridization under stringent conditions showed a strong signal intensity of the 2.5 kb and 2.7 kb Hind III fragment in a Southern blot of genomic DNA. Preliminary dam using different regions of the PADPRP cDNA as a probe to Hind III restricted genomic DNA of the A and B genotypes indicated that the sequences on chromosome 13 were linear with respect to the cDNA and probably represented a processed pseudogene (Cherney et al., Proc. Natl. Acad. Sci. USA 84:8370-8374 (1987); and unpublished observations).

A chromosome 13-enriched library of Hind III fragments (see Materials and Methods) was therefore screened using full-length cDNA to human PADPRP. The entire sequence of one of the genomic clones was determined, and found to be the expected Hind III fragment of 2682 base pairs. An earlier analysis of the polymorphic Hind III alleles had estimated the sizes to be 2.8 kb and 2.6 kb for the A and B genotypes respectively (Bhatia et al., Cancer Res. 50:5406-5413 (1990)). Genomic DNA from cell lines previously identified as representing either the A allele (lane 1) or B allele (lane 2) were restricted with Hind III and compared to the isolated clone (lane 5) after Southern blotting (FIG. 1). A direct size comparison between the cloned genomic fragment to the A and B genotypes showed that the isolated clone represented the Hind IIIA allele. We therefore correct our original Hind III allelic combination and report them as 2.7 kb (A allele) and 2.5 kb (B allele). The chromosome 13 origin of the isolated Hind III clone was verified by hybridization to a human-mouse cell hybrid PGME1 (Mitchell et al., Oncogene 4:253-7 (1989)) containing an intact chromosome 13 (Lane 4, FIG. 1). This cell hybrid was found to have the PADPRP B genotype. The hybridization signal did not represent the endogenous mouse PADPRP gene as there was no hybridization to mouse spleen DNA (Lane 3, FIG. 1).

To determine the relationship between the Hind III clone (A allele) and the cDNA-encoding the authentic PADPRP protein (Cherney et al., Proc. Natl. Acad. Sci. USA 84:8370-8374 (1987)), the nucleotide sequences were aligned as shown in FIG. 2. Sequence analysis revealed an overall shared identity of 91.79% between the PADPRP A allele and the cDNA (FIG. 2). The resemblance of the cloned fragment to an intronless cDNA copy as well as the high sequence identity to the cDNA suggest that the PADPRP sequences on chromosome 13 exist as a processed pseudogene (Weiner et al., Annu. Rev. Biochem. 55:631-661 (1986)). The genomic clone retained the Hind III site found on the cDNA sequence (nt 887, lower sequence from FIG. 2), and also encompassed a region which extended into the corresponding 3' non-coding portion of the cDNA (protein terminates at TAA nt 3233-3235, FIG. 2). Restriction enzymes (such as Eco RI and MspI) which were earlier found to be informative for detecting the PADPRP polymorphism therefore have sites outside the duplicated region. BamHI did not detect the original polymorphism since this restriction site is found within the duplicated sequences (nts 896 and 1089, FIG. 2). A schematic representation of the Hind III genomic clone (A allele) and its relationship to the functional domains of the PADPRP protein is depicted in FIG. 3.

EXAMPLE 8

PADPRP gene on chromosome 13 has a repeated 193 base pair region

Alignment of the Hind III clone to the cDNA revealed eight gaps, of which the most significant was a 193 bp gap in the cDNA sequence commencing at bp 1825 (FIG. 2). This gap reflected a duplication of a 193 bp sequence in the A allele which was not found in the cDNA. Inspection of the sequences around the duplicated region showed a 9 bp repeat at the beginning and flanking the 3' end (with two gaps) of the duplicated region (nts 747–755 and nts 1133–1143 from FIG. 2). It was therefore possible that an alteration in the processed pseudogene structure occurred as a result of DNA looping during replication.

To provide insight into the evolutionary relatedness between the duplicated regions, the sequences of each 193 bp region of the A allele (nts 747–939 and nts 940–1132) were compared to the homologous sequences of the PADPRP cDNA as illustrated in FIG. 4. This comparison showed that among the duplicated 193 bp regions there were only two nucleotide alterations, while we observed six and eight nucleotide changes respectively, between each 193 bp region and the cDNA. As derived from FIG. 2 there was an overall 8.2% nucleotide difference between the PADPRP processed pseudogene on chromosome 13 and the DNA, while only a 1.0% divergence between the duplicated regions (from FIG. 4). Thus, it appears as if the duplication of PADPRP related sequences on chromosome 13 was of a recent occurrence compared to the integration and formation of the PADPRP processed pseudogene on the q arm of chromosome 13. No other duplicated or inverted sequences were observed in the cloned Hind III fragment.

EXAMPLE 9

Verification of the nature of the PADPRP B allele

Since size analysis in agarose gels after restriction with various enzymes produced an approximate 200 bp difference between the A and B allele, and the duplicated region in the sequenced Hind IIIA allele was determined to be 193 bp (FIG. 2 and Bhatia et al., *Cancer Res.* 50:5406–5413 (1990)), it seemed reasonable to assume that the B allele reflected the non-duplicated version of the PADPRP sequences on chromosome 13. To determine if this hypothesis was correct, oligonucleotide primers which flank the duplicated region were utilized in a PCR (containing nts 636 to 1230 of the Hind III clone) to amplify genomic DNA. Synthetic oligonucleotides (overlined in FIG. 2) were designed to exploit the sequence differences between the PADPRP processed pseudogene (13q33->qter) and the PADPRP active gene (1q42). In addition, the primers selected for the PCR amplified a region of the PADPRP gene on chromosome 1 which encompassed an intron, and could be distinguished from the processed pseudogene (chromosome 13) by a difference in DNA size.

Figure 5:
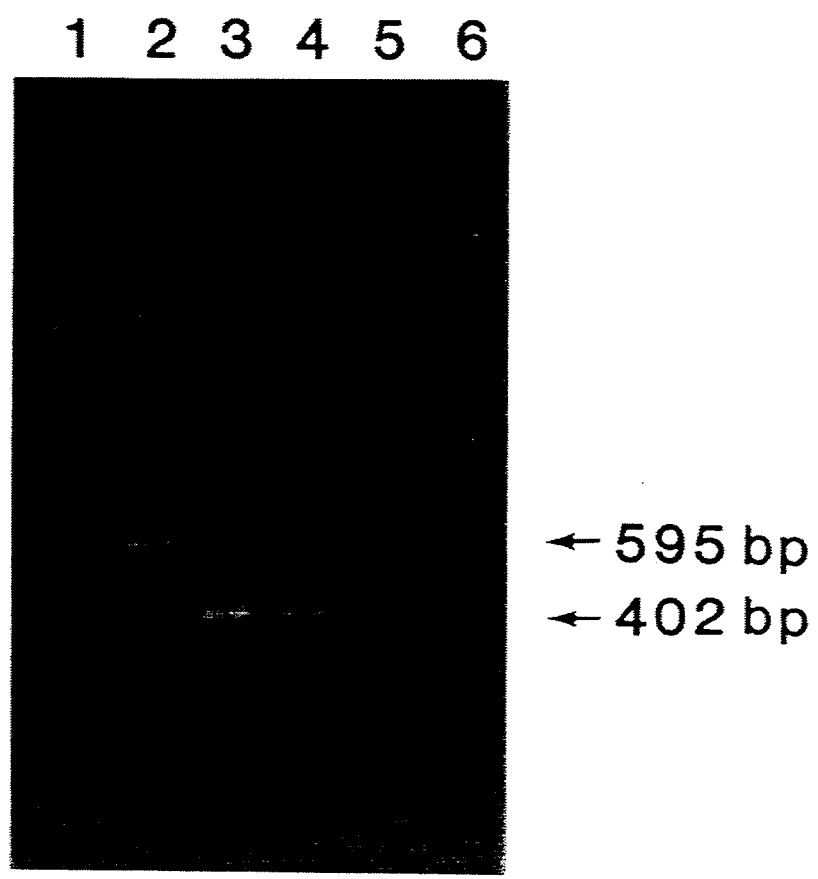
FIG. 5: Ethidium bromide stain of a 1.5% agarose gel of the amplified PCR products. Lane 1 contains the 1 kb ladder (BRL). The amplified DNA depicted are from individuals of the PADPRP A genotype (lane 2), B genotype (lane 3) or AB genotype (lane 4). Lane 5 is the control reaction using full-length cDNA (pCD12) as described by Cherney et al., *Proc. Natl. Acad. Sci. USA* 84:8370–8374 (1987), while lane 6 represents amplified DNA from the Hind III 2.68 kb clone in pBluescript.

Germ line DNA from individuals with prostate cancer whose PADPRP genotype had been previously determined by Southern blotting (Table 7) was used in the PCR. FIG. 5 shows that the amplified DNA yielded only the expected size for patients who had a PADPRP AA genotype (595 bp, lane 2), BB genotype (402 bp, lane 3) or AB genotype (lane 4). Lane 5 represents the control reaction in which the PADPRP cDNA-encoding the authentic protein is used as the template. As shown in FIG. 5 the designed primers did not amplify the PADPRP sequences from chromosome 1. Amplified DNA from the Hind III 2.68 kb clone in pBluescript is shown in lane 6. Furthermore, the PADPRP gene on chromosome 14 was not amplified, as a common DNA fragment, independent of the PADPRP genotype (see FIG. 5) would be expected from the PCR. These data indicated that mismatches at the 3' end of the primers as well as the internal mismatches were sufficient to prevent amplification of related PADPRP sequences.

The 402 bp (B allele) PCR product (FIG. 3) was sequenced and found to contain the non-duplicated version of the PADPRP sequences. Alignment of this sequence with the cloned Hind Ill A allele uncovered one nucleotide difference (G replaced by A) between the amplified DNA and the second 193 bp duplicated region (FIG. 3). This nucleotide difference was unlikely to be the consequence of an error in AmpliTaq polymerase, since identical sequences were also found in amplified germline DNA from two other individuals having the B allele genotype. Thus, the observed polymorphism associated with the PADPRP sequences on chromosome 13 was attributed to a duplicated 193 bp sequences within the processed pseudogene.

EXAMPLE 10

Use of the PADRP B Allele As A Marker For Cancer

The increased frequency of the B allele observed in black patients with multiple myeloma, prostate and colon cancer compared to the appropriate racial control group suggest that the PADPRP polymorphism is a valid marker for a predisposition (along with other genetic markers) to these cancers. However for black patients with lung and breast cancer, the frequency of the B allele was not statistically different from the non-cancer population. Among white patients with multiple myeloma, prostate or lung cancer, the PADPRP polymorphism did not correlate with a germline derived increase of the $\beta$ genotype. Our observations contrast with the previous study in which a tumor associated increase in the B allele frequency (greater than twofold) was found in $\beta$-cell lymphoma and lung carcinoma but not in myeloid leukemia from white individuals (Bhatia et al., *Cancer Res.* 50:5406–5413 (1990)). These data imply that the PADPRP polymorphism associated with a predisposition to cancer, may be confined to, specific diseases that are dependent on the racial population under study.

We were thus prompted to clone and characterize the PADPRP-like sequences on chromosome 13 associated with a predisposition to cancer. A 2.68 kb genomic clone was isolated and sequenced, which represented the Hind IIIA allele of the PADPRP processed pseudogene (FIG. 1). This is the predominant PADPRP genotype in noncancer individuals (Table 7). The characteristics of a processed pseudogene include features such as a lack of introns and the presence of a poly (dA) tail at the 3' end (Weiner et al., *Annu. Rev. Biochem.* 55:631–661 (1986)). However, the absence of a poly (dA) tail in the Hind III fragment suggests that the genomic clone isolated in this study does not represent the entire PADPRP processed pseudogene on chromosome 13.

The most unexpected observation was the identification of a 193 bp duplication within the PADPRP sequences which was responsible for the differences between the A/B polymorphism. The dam relating the RFLP A/B polymorphism with the newly detected 193 bp duplication were confirmed in a PCR assay in which primers were developed to discriminate the processed pseudogene from other PADPRP related sequences. The PCR also provides a relatively easy method for screening the genotype of a large number of individuals at high risk for certain cancers over Southern blotting. Thus, we have identified the source of the RFLP associated with a predisposition to cancer in a selected population.

The 8.21% divergence in nucleotide sequence between the PADPRP (A allele) and the cDNA (derived from FIG. 2) suggests that the integration of the processed pseudogene into chromosome 13 was not a recent event. In this context, a comparison of the noncoding sequences of the β-globin gene of human and chimpanzee suggests that nucleotide changes accumulate at an approximate rate of 0.3% per million years (Maeda et al., Proc. Natl. Acad. Sci. USA 80:5012–5016 (1983)). This allowed us to estimate that the processed pseudogene is probably at least 27.3 million years old. Other studies show that the noncoding 5' and 3' flanking, as well as other polymorphic regions of the very conserved Ψη-globin pseudogene sequences differ by 1.61–1.84% between human and African apes. This latter observation placed a species divergence as occurring between 4.7–7.1 million years ago (Miyamoto et al., Science 238:369–239 (1987); Miyamoto et al., Proc. Natl. Acad. Sci. USA 85:7627–7631 (1988)). Taken together, our data suggest that the integration of the PADPRP (cDNA-like) sequences at the 13q33-qter locus occurred before the human/great ape divergence, and we favor the possibility that a PADPRP processed pseudogene may be present in the African apes (supported by preliminary dam, unpublished observation). In contrast, the duplicated PADPRP sequences on the A allele showed a lower degree of overall nucleotide divergence (1.04%, derived from FIG. 4). Thus, the B allele probably represents the primordial gene, and the duplication of this region occurred considerably after the initial integration on chromosome 13. Since 0.5–1.0% of the human genome is estimated to be polymorphic (Cooper et al., Hum. Genet. 69:201 (1985)), our observations are consistent with the suggestion that the A allele only occurs in humans.

TABLE VII

Frequency of the B Allele In Germline DNA From Patients With Various Cancers

| Cancer Type | Race | Genotype AA | AB | BB | Total | B Allele Frequency |
|---|---|---|---|---|---|---|
| Multiple Myeloma | Black | 5 | 11 | 15 | 31 | 0.66 |
|  | White | 28 | 7 | 2 | 37 | 0.15 |
| Prostate | Black | 1 | 3 | 5 | 9 | 0.72 |
|  | White | 10 | 6 | 0 | 16 | 0.19 |
| Lung | Black | 1 | 5 | 3 | 9 | 0.61 |
|  | White | 4 | 4 | 1 | 9 | 0.33 |
| Colon | Black | 0 | 8 | 3 | 11 | 0.64 |
| Breast | Black | 12 | 7 | 2 | 21 | 0.26 |
| Control: non-cancer population | Black* | 15 | 18 | 4 | 37 | 0.35 |
|  | White* | 45 | 12 | 2 | 59 | 0.14 |

Germline DNA was obtained from peripheral blood lymphocytes, restricted with HindIII and hybridized with a full-length PADPRP probe aftger Southern blot analysis. Designation of the genotypes is as described by Bhatia et al., 1990.
*Distribution of genotypes in these groups were taken from Bhatia et al., 1990.

EXAMPLE 11

Potential significance of the duplicated region

To address how the polymorphic PADPRP sequences on chromosome 13 may be linked to a predisposition to certain cancers, two possible explanations emerge from an analysis of the processed pseudogene. Although processed pseudogenes are generally regarded as nonfunctional (Weiner et al., Annu. Rev. Biochem. 55:631–661 (1986)), recent studies have provided evidence that gene transposition plays an important evolutionary role in the development of diseases such as acholinesterasemia, hemophilia A and neurofibromatosis (Muratani et al., 1991; Dombroski et al., 1991; Wallace et al., Nature 353:864–866 (1991)). Of potential significance, the duplicated sequences represented the most conserved area (96.4% average sequence identity, derived from FIG. 2) between the PADPRP processed pseudogene and the cDNA. FIG. 6 shows the predicted amino acid sequence of the only long open reading frame (ORF) in the isolated Hind III clone from chromosome 13. In the A allele, the duplicated region would allow the introduction of a unique methionine residue, which is absent in the B allele. The authentic PADPRP protein has been implicated to play a role in DNA recombination, replication and repair; processes which are involved in tumorigenesis. In this regard, if the A allele were to encode a functional protein, it would correspond to the C-terminal portion of the automodification domain of the PADPRP gene, and as such, would be highly homologous over a sixty-five amino acid region (underlined in FIG. 6) with only one conservative valine for alanine replacement. In addition, this protein would contain a homologous region of approximately seventy amino acid residues whose biochemical function with respect to the catalytic activity of PADPRP is unknown. The close sequence similarity between this potential protein from the A allele and the automodification domain of the authentic PADPRP protein may suggest an intolerance for amino acid change, and could be an indication of functional similarity. This putative protein might therefore compete with the active polymerase for ribosylation sites at DNA strand breaks. Thus, it is seductive to speculate that the A allele may encode a protein product, not present in the B allele, which is related to a decreased susceptibility to certain cancers. Future efforts will be directed at determining if this region is transcriptionally active. It is interesting that all the DNA samples from endemic Burkilts lymphoma (a pediatric cancer) contained at least one copy of the B allele (Bhatia et al., Cancer Res. 50:5406–5413 (1990)). Hence, duplication of specific sequences to form the A allele could result in a selective evolutionary advantage for avoiding a childhood (versus late adult) cancer.

Another possible consideration is that the B allele may cosegregate with another gene whose function, or lack of, contributes to the development of malignancy. Furthermore, our observations do not dispute the fact that other genetic changes such as small deletions or point mutations of a nearby gene may be linked to the PADPRP polymorphism. Since the integration of PADPRP related sequences on chromosome 13 occurred millions of years ago, this linkage must be close to the processed pseudogene, otherwise a crossover event would have occurred to separate distally linked genes. In this regard, we previously identified a Pst I RFLP (7.2/5.3 kb allelic fragments) which cosegregated with the Hind III RFLP, and was initially thought to reflect the same duplication detected by Hind III (Bhatia et al., Cancer Res. 50:5406–5413 (1990)). Sequence analysis reveals no Psi I sites within the Hind III 2.7/2.5 alleles demonstrating that the Psi I polymorphism is independent of the RFLP detected by Hind III. We are now analyzing whether the genetic change detected by Pst I is a better predictor of a predisposition to cancer.

In summary, a genomic Hind III 2.68 kb clone was successfully isolated and found to encompass the PADPRP polymorphic sequences at the q33->qter region on chromosome 13. These sequences provide an anchor point for a rewarding study directed at elucidating the genomic structure of the distal end of 13q.

EXAMPLE 12

Construction of a recombinant phage library enriched for human chromosome 13
Screening and isolation of the PADPRP-related sequences The Charon 40 library was screened using a HindIII 2.68 kb fragment which represented part of the PADPRP sequences on chromosome 13 (Lyn et al. 1993). Approximately 30,000 phage were screened under stringent hybridization and wash conditions.
DNA Subcloning and sequencing To facilitate sequencing of the genomic clone, two overlapping fragments (an EcoRI 5.3 kb and PsII 7.4 kb) derived from one bacteriophage isolate were subcloned into the appropriately digested pBluescript (Stratagene). The DNA was sequenced by the dideoxynucleotide chain-terminating method (Sanger et al. 1989) using Sequenase (U.S. Biochemical). Initially, the 5' and 3' termini of the clones were determined using primers to the T3 and T7 promoter regions. The entire sequence was determined on 98% of both strands by using a series of oligonucleotides obtained from the sequential reaction.
Sequence Analysis The database computations were accomplished using fasta (University of Wisconsin Genetics Computer Program) and the BLAST network service (National Center for Biotechnology Information).
Other Methods Southern blotting and hybridization conditions were performed as described by Bhatia et al. 1990. Germline DNA was isolated from peripheral blood lymphocytes as previously described (Bhatia et al. 1990).

Results

Isolation and analysis of the PADPP gene on chromosome 13

To obtain the complete PADPRP gene on 13q34, a chromosome 13 enriched library was screened using a HindIII 2.68 kb probe that represented the polymorphic PADPRP sequence (Lyn et al., 1993). Three positive phage clones were initially isolated, of which one clone contained fragments (2.7 kb Hind III and 5.3 kb EcoRI) known to represent the PADPRP sequences on 13q (Bhatia et al. 1990) when analyzed by Southern blotting (data not shown). FIG. 14 depicts a genetic map of a 9.3 kb EcoRI/PstI genomic region showing the position of the entire PADPRP gene (3.77 kb). The isolated PADPRP sequences in this study contained a 193 bp duplicated region, and thus represented the PADPRP A allele.

Figure 7:
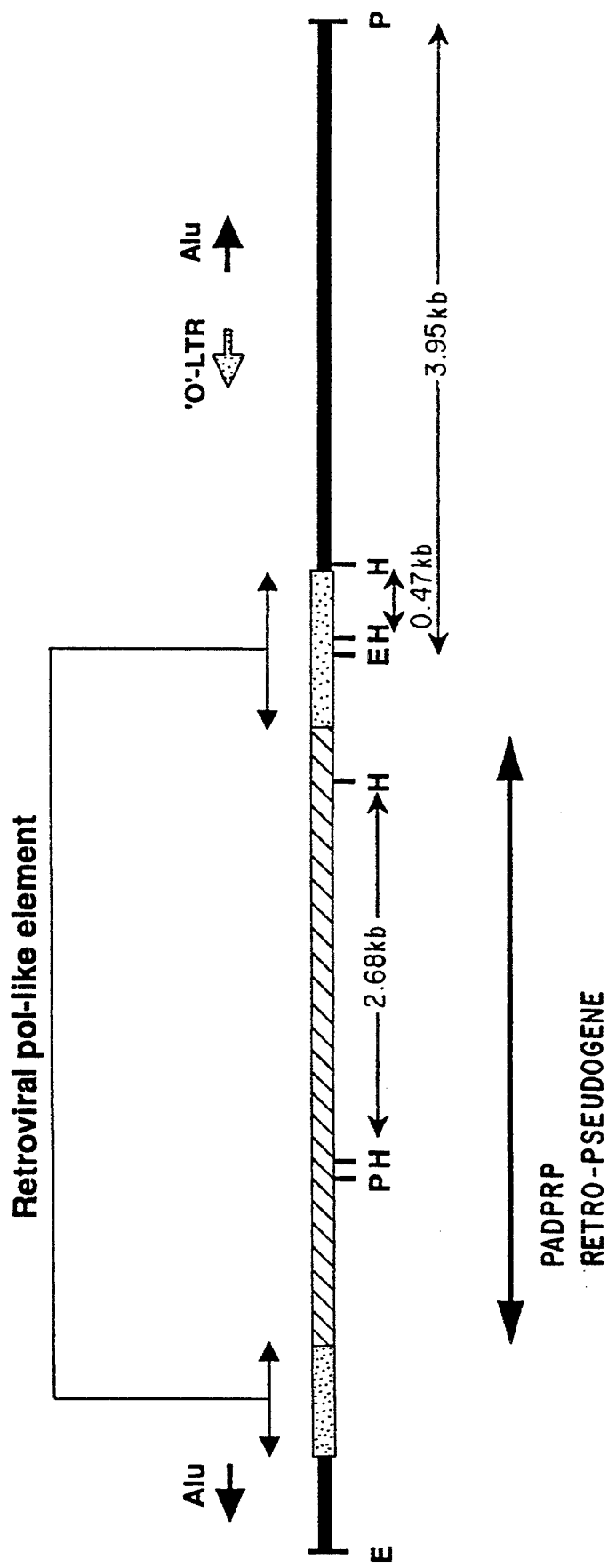
FIG. 7: Genetic map of a 9.3kb EcoRI/PstI genomic region showing the position of the entire PADPRP gene (3.77 kb).
Figure 8:
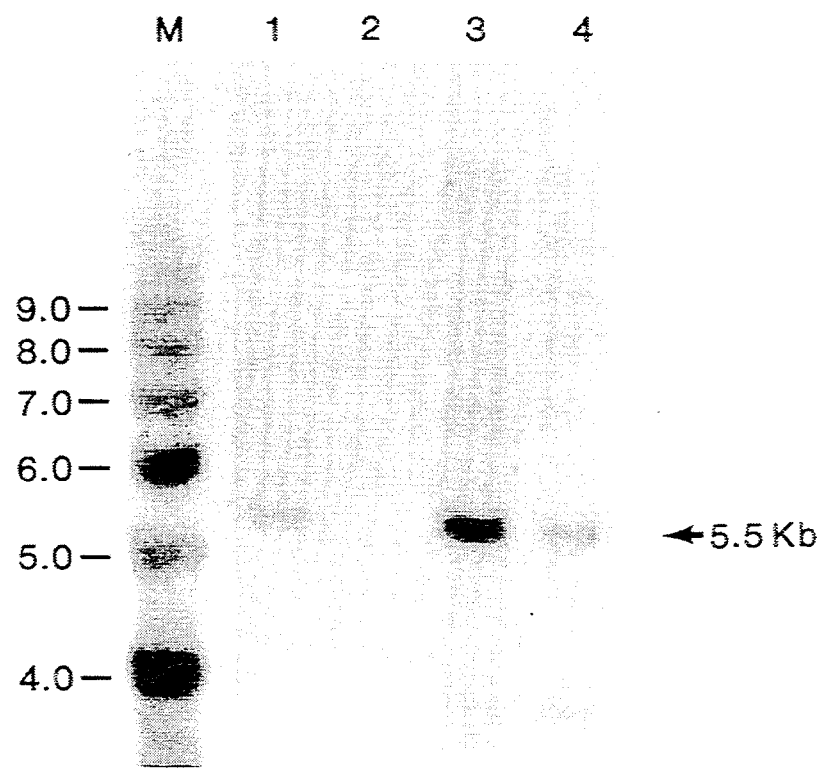
FIG. 8: Southern blot using a 0.47 kb fragment (see FIG. 7) as a probe.

To verify the chromosome 13 origin of the genomic clone, a 3.9 kb EcoRI/PstI fragment encompassing the non-PADPRP related sequences (see FIG. 7), was initially used to probe a human-mouse cell hybrid containing an intact chromosome 13. High stringency hybridization conditions produced smears in a Southern blot (data not shown). This result provided a clue that the genomic region downstream of the PADPRP gene included common repetitive sequences. When a smaller fragment (0.47 kb HindIII, FIG. 7) was used as a probe, discrete bands were identified after hybridization to a cell hybrid DNA containing an intact chromosome 13 (FIG. 8). The hybridization signal did not represent the mouse PADPRP gene, as there was no hybridization to DNA from mouse spleen (FIG. 8). This non-PADPRP related probe detected an EcoRI fragment (5.6 kb) when hybridized to genomic DNA from cell lines representing either the PADPRP A or B genotype (lanes and respectively, FIG. 8).

To determine the relationship between the PADPRP sequences (13q34) and the cDNA encoding the authentic PADPRP protein (Cherney et al. 1987), the nucleotide sequences were analyzed and found to exhibit an overall sequence identity of 91.8%. The PADPRP sequences also included 136 bases of the homologous 5' untranslated region, and had a lower sequence similarity (78.0%). Features which are characteristic of nonviral retro-pseudogenes such as a close resemblance to a mRNA species, lack of introns and a short poly (A) tail at the 3' end (Weiner et al. 1986) were displayed by the isolated PADPRP gene. Upon integration into a new genomic site, it is thought that nonviral retroposons generate short repetitive sequences (7–21 bp) of host DNA (Daniels and Deininger, 1985). No recognizable direct repeats were found immediately flanking the PADPRP retro-pseudogene. This suggested that the retro-pseudogene was inserted at a blunt end site. Alternatively, since the integration of PADPRP sequences at the 13q34 locus was estimated to have occurred at least 27 million years ago (Lyn et al., 1993), the direct repeats may have been lost through mutation. In the course of analyzing the PADPRP sequences, we observed that the retro-pseudogene was inserted within a truncated retroviral element (see below).
Endogenous pol-like element To define the nucleotide sequences adjacent to the PADPRP retro-pseudogene, a computer assisted comparison of these sequences to the databases revealed a homology to only the pol gene of various endogenous retroviral sequences. No homology was detected to sequences which represent gag, env or long terminal repeat regions (LTR) usually found in endogenous and exogenous retroviruses. The pol-like viral DNA sequences encompassed 1535 bases (Sequence ID No. 8). To determine the evolutionary relatedness between this pol-like element and other endogenous retroviruses, an alignment of these sequences revealed a nucleotide similarity of 60%–62% to a family of retrovirus-like elements named RTVL-I ([retrovirus-like sequence isoleucine] Maeda and Kim, 1990). On the other hand, the 3' region (860–890 bases) of this pol-related element displayed a more distant relationship (53–55% similarity) to other human endogenous retroviral sequences (La Mantia et al. 1991; Steele et al., 1985). The solitary pol-like element was unlikely to represent the truncated endogenous retrovirus tentatively assigned to chromosome 13, that was thought to have a LTR-gag-pol structure (Steele et al. 1986). Moreover, a related truncated retroviral element (clone 51-1, Repaske et al. 1983) showed a 54.3% nucleotide identity over 7 bases when aligned to this newly identified pol-like DNA segment.

To assign presumptive functional domains to the endogenous virallike element, the reading frame was adjusted to maintain a co-linear amino acid sequence (data not shown), which was then compared to the coding region of endogenous and exogenous retroviruses. The genomic viral-like sequences contained some twenty-two amino acids before the potential start of a pol-like encoding region. Although a potential gag-pol boundary was ambiguous from the deduced amino acid sequence, the viral-like element contained the sequence Gly-Asn-Gln-Gly that was similar to the start of the pol protein (Gly-Gly-Gln-Gly) from Moloney murine leukemia virus (Shinnick et al. 1981). The PADPRP retro-pseudogene was integrated 638 bases from the start of the endogenous viral-like sequences. Immediately downstream of the PADPRP sequences, the deduced amino acids of the pol-like element were found to retain the functional domains of a putative RNA-dependent polymerase. A highly conserved region of five motifs have been identified among reverse transcriptase encoding elements (Poch et al. 1989). FIG. 9 showed that 20 out of 26 potential amino acids within this conserved region were retained in a similar linear arrangement, when aligned to other retroviral pol encoding residues. In addition, a comparable distance separating each motif was maintained. Altogether, this endogenous retroviral-like element represented a truncated pol gene in which the 3' endonuclease and DNA-binding domains (Toh et al. 1983) were absent.

Figure 10:
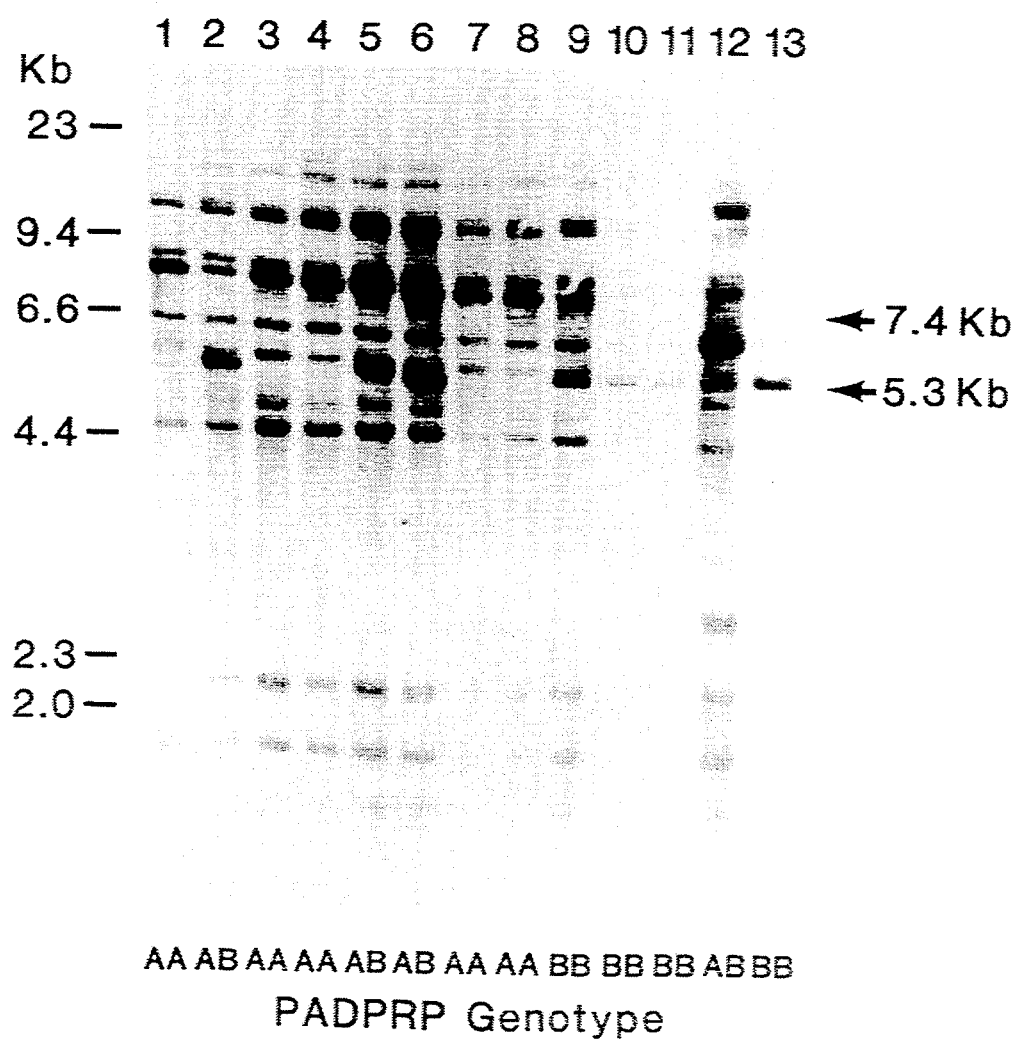
FIG. 10: Southern blot of total human DNA using a 0.47 kb probe (see FIG. 7).

To assess the relative abundance of the endogenous pol-like element in the human genome, a 0.47 kb HindIII probe (see FIG. 7) identified at least ten discrete bands when hybridized to PsII digested germline DNA of eight unrelated individuals (FIG. 10). This probe represented part of the reverse transcriptase-like encoding fragment. A similar pattern of hybridization was observed between Caucasians and African-American blacks. However, the relative intensity of the bands varied between individuals, indicating a higher copy number of viral sequences were integrated in the germline. This may have arisen either by multiple insertions during a retroviral infection(s), or by duplication and dispersal of the original viral-like element.

Repetitive sequence elements

Two complete Alu sequences as well as a transposon element from the 'O'-family were identified within the EcoRI-PstI genomic region as illustrated in FIG. 6. Alu elements represent one of the most abundant repetitive DNA sequences in the human genome, and are derived from a dimeric 7SL RNA (Weiner et al. 1986). The two Alu elements were separated by 7.3 kb, in reasonable agreement with their expected distribution of one element every 5 kb in the human genome. A comparison of each Alu sequence to the data bank showed a nucleotide identity of 90.0% and 88.0% (Alu element upstream and downstream of the endogenous retro-viral element, respectively) to a representative (HS G18N1) of the Human Specific (HS) subfamily of Alu elements (Batzer et al. 1990). The HS Alu subfamily members are believed to represent a recently inserted group of Alu elements with the human genome. Inspection of the flanking nucleotide sequences of these repetitive elements revealed an AT composition of 46–78% (Table VIII), consistent with previous data on the sequence specificity observed at the integration site of Alu and other repetitive elements (Batzer et al. 1990).

An inverted element of the 'O'-family of repetitive sequences was positioned 1.14 kb downstream of the reverse transcriptase-like sequences. The 'O'-family represent a class of transposon elements which share structural features to long terminal repeat (LTR)like elements, and are moderately repeated within the human genome (Paulson et al. 1985). The sequenced 'O'-0LTR element in the isolated genomic clone began with the expected 5'-TG ... and ended with ... CA-3', and was flanked by a 9 bp direct repeat (see Table 8). Alignment of the 'O'-LTR sequences to other sequenced 'O' family members showed a 74.5% nucleotide similarity to a human clone (O-5) described by Sun et al. 1984, and a 80.1% similarity to an isolated clone derived from African green monkey DNA.

Homology to other genes

A sequence comparison of the genomic region between the pol-related sequences and the 'O'-like element showed a 66.0% nucleotide identity over 250 bases to an expressed sequence tag gene (EST02291) of unknown function (Adams et al. 1992). No open reading frames were detected within these DNA sequences. This result may be interpreted as indicating that these sequences represent a pseudogene to either the expressed sequence tag, or to a closely related gene of the expressed sequence tag. Further sequence comparisons of the genomic segments between the pol-related segment and the repetitive elements revealed no significant homology to any sequence listed in the data bank.

Discussion

This report describes the successful utilization of a chromosome 13 enriched Charon 40 library (LANL1301) to isolate the entire PADPRP-like sequences (13q34). It is expected that this chromosome 13 library will be a source for isolating other chromosome 13 specific DNA markers. The PADPRP gene was recovered as a full-length cDNA-like copy and included 136 bases of the homologous untranslated region. It had an overall nucleotide identity of 91.8% to the cDNA derived from chromosome 1. Since non-coding regions generally accumulate mutations faster than coding sequences, it was not unexpected that the homologous 5'-untranslated region of the PADPRP cDNA exhibited a lower similarity (78.0%) to the retropseudogene on 13q34. The isolated PADPRP gene in this study represented the A allele as it included a direct repeat of 193 bases, which was previously identified as the source of the PADPRP polymorphism (Lyn et al. 1993). Altogether, the sequenced EcoRI/PstI genomic clones provide an anchor point for genetic mapping a region on chromosome 13 which has a low density of DNA markers.

An endogenous, truncated pol-related element was identified that included sequences similar to a reverse transcriptase encoding element. The PADPRP retropseudogene was inserted within these newly identified pol-like sequences. This solitary pol-like element represented unique sequences which differed by at least 40% from other reported endogenous retroviruses (Repaske et al. 1985; Maeda and Kim, 1990; La Mantia et al. 1991). Multiple but discrete bands were observed when a fragment of the reverse transcriptase-like element was used to probe restricted genomic DNA (FIGS. 8 and 10). This suggested that the pol-like element was part of a family of vital-like sequences which were integrated at multiple chromosomal locations. It is unknown if they represent a family of novel truncated pol-like elements, or whether they include complete retroviral DNA sequences. The truncated retroviral-like DNA segment may have arisen from the incomplete reverse transcription of an exogenous virus during the replicative process. Another possibility was that these pol-like sequences evolved from a common ancestral polymerase element which was subsequently dispersed throughout cellular organisms as has been suggested by Temin, 1989.

Integration of the repetitive elements at the 13q34 locus probably occurred as independent events, since direct repeats were found bordering each fragment. The Alu elements exhibited a lower degree of divergence (average 89.0%) from other family members compared to the 'O'-LTR elements (74.5%). This suggested that the 'O'-LTR element was inserted prior to the integration of the other retroposons.

The 13q34 locus appears to be a recipient genomic site for retroposons, implying that this region may be prone to recombination as retroposition requires a chromosome break followed by integration of the retroposed fragment. The PADPRP retro-pseudogene represents a polymorphic marker which is believed to be associated with a predisposition to cancer. We have speculated that the PADPRP sequences may co-segregate with an unknown gene which is involved in the development of malignancy (Lyn et al. 1993). Thus if this chromosomal site is transcriptionally active, an open double-strand DNA and chromatin structure may have allowed access to a recombinase-mediated translocation of a mRNA-like copy or repetitive element. Retroposons as well as viral-like genomic sequences have been viewed as parasitic DNA (Doolittle et al. 1980). On the other hand, retroposition offers the opportunity to generate genetic variability through DNA recombination and rearrangements that provides material for natural selection to act on. It will be interesting to analyze the homologous genomic regions of non-human primates towards gaining a molecular picture of primate evolution.

| Repetitive element Orientation | Location | Flanking repeats | |
|---|---|---|---|
| | | Length | Sequence |
| Alu inverted | 175–475* | 12 | GAACCAGGACAG |
| 'O'-like inverted | 6995–7319 | 9 | ATCTTATCTG |
| Alu direct | 7779–8086 | 9 | AACAACAACTA T |

*Numbers refer to the nucleotide position with respect to the 5'EcoRI site (FIG. 1). The location of the nucleotide positions exclude the repeats bordering the repetitive elements.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

AAGAAGCCAA CATCTGAGCT                                                                     20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TTTCCTTGTC ATCCTTCAGC                                                                     20

( 2 ) INFORMATION FOR SEQ ID NO:3:

( i ) SEQUENCE CHARACTERISTICS:
        ( A ) LENGTH: 2682 base pairs
        ( B ) TYPE: nucleic acid
        ( C ) STRANDEDNESS: both
        ( D ) TOPOLOGY: linear ( i i ) MOLECULE TYPE: DNA ( x i ) SEQUENCE DESCRIPTION: SEQ ID NO:3:

AAGCTTGAAA AGGCCCTAAA GGCCCAGAAC GACCTGATCT GGAACATCAA GGACGAGCTA    60

ATGAAAGTGT GCTCTATTAA TGACCTGAAG GAGATGCTCA TCTTCAACAG GCAGCAGGTG    120

CCTTCCGGGG AGTCGGCGAT CTTGGACCGA GTAGCTGACA GCATGACGTT CGGTGCCCTC    180

```
CTTCCCTGTG  AGGAATGCTC  AGGTCAGCTG  GTCTTCAAGA  GCGACACTTA  TTACTGCACC   240
GGGGACGTCA  CGGCCTGGAC  CAAGTGTATG  GTCAAGACAT  GGACACCCAA  CCAGAAGGAA   300
TAGGTGATCC  CACCGAGAAA  TCTCTTAACT  CAAGAAATTT  AAGGTTAAAA  AGCAGGACCG   360
TATATTTCCC  CCAGAAACCA  GTGACCCAGT  GGCGGCCATG  CCCCCACCCT  CCACAGCCTC   420
CGAGCCTGCT  GCCATGAACG  CCTCTGCTCC  AGCAGATAAG  CCGTTATCCA  ACATGAAGAT   480
CCTTACTCTT  GGGAAGCTCT  CCCGGAACAA  GGATGAAGTG  AAGGCCACGA  TTGAGAAACT   540
CGGGGGAAAG  TTGATGGGGA  CGGCCAACAA  GGCTTCTCCG  TGCATCAGCA  CTAAAGAGGA   600
GGTGGAAAAG  AAGAAGAAGA  AGATGGAGGA  AGTGAAAGAA  GCCAACATCT  GAGCTGTGTC   660
TGAGGACTTC  CTCCAGGACT  TCTCTGCCTC  CACCAAGGGG  CTCCAGGAGT  TGTTCTCAGC   720
GCACATATTG  ACCCCTGGG  GGGCAGAGGT  GAAGGCAGAG  CCTGTTGAAG  TCGTAGCCCC   780
AAGAGGGAAG  TCAGGAGCTG  TGCTCTCCAA  AAAAGCAAG  GGCCAGGTCA  AGGAGGAAGG   840
TATCAACAAA  TCTGAAAAGA  GAATGAAATT  AACTCTTAAA  GGAGGAGCAG  CTGTGGATCC   900
TGACTCTGGT  CTGGAACACT  CTGCGCATGT  CCTGGAGAAA  GGTGAAGGCA  GAGCCTGTTG   960
AAGTCGTAGC  CCCAAGAGGG  AAGTCAGGAG  CTGTGCTCTC  CAAAAAAGC  AAGGGCCAGG  1020
TCAAGGAGGA  AGGTATCAAC  AAACTGAAAA  AGAGAATGAA  ATTAACTCTT  AAAGGAGGAG  1080
CAGCTGTGGA  TCCTGACTCT  GGTCTGGAAC  ACTCTGCACA  TGTTCTGGAG  AAAGGTGGGA  1140
AGGTCTTCAG  TGCCACCCTC  AGCCTGGTGG  ACGTCGTTAA  GGAACCAAC  TCCTATTACA  1200
AGTGAAGTTT  GCTGAAGGAT  GACAAGGAAA  GCAGGCATTG  GATATTCAAG  TCCTGGGACC  1260
GTGTGGGCAC  GGTGATCGGT  AGCAACAAAC  TGGAACAGAT  GCTGTCCAAG  GAGGACACCA  1320
TTGAACACTT  CATGAAATTA  TATGAAGAAA  AACTAGGAAT  GCTTGGCACT  CCAAAAATTC  1380
ACAAAGTATC  CCAAAAAGTT  CTACCCCCTG  GAGATTGACT  ACGGCCAGGA  CAAAGAGGCG  1440
GTGAAGAAGC  CGACAGTAAA  TCCTGGCACC  AAGTCCATGC  TCCCCAAGCC  AGTTCAGGAC  1500
CTATCAAGAA  TGATCTTTGA  TGTGGAAAGT  ATGGCAAAGG  CCCATGGGGG  GTGTGAGATC  1560
AACCTTCAGA  TGCCCTTGGG  GAAGCTGAGC  AAAAGGCAAA  TCCAGGCCGC  GTACTCCATC  1620
CTCAGGTCCA  GCAGGTGGTG  TCCCAGGGCA  GCAGCGACTC  TCAGATCCTG  GATCTCTCAA  1680
ATCGCTTTTA  CATCCTGATC  CCCCACGACT  TTGGGATGAA  GGATCCTCTG  CTCCTGAACA  1740
ATGCAGACAG  TGTGCAGGCC  AAGGTAGAAA  TGCTGGACAA  CCTGCTGGAC  ATTGAGGTAG  1800
CCTACGGTCT  GCTCAGGGGA  GGGTCTCACG  ATAGCAGGAA  GGACTCCATC  GATGTCAACT  1860
ATGAGAAGCT  CAAAACTGAC  ATTAAGGTGG  TTGACAGAGA  TTCTGAAGAA  GCTGAGATCA  1920
TCAGGAAGTA  TGTTAAGAAC  ACTCATGCAA  CCAACCACAC  ACGATGCATA  TGACTTGGAA  1980
GTCATTGATA  GCTTTAAGAT  AGAGTGTGAA  GAGGAGTGCC  AGCACTACAA  GCCCTTTAAG  2040
CAGCTTCATA  ACTGAAGGTT  GCTGTGGCAT  GGGTCCAGGA  CCACCAACTT  TGCTGGGATC  2100
CTGTCCCTGG  GTCTTTGGAT  AGCCCTGCCT  GAAGCACCTG  TGATGGGCTA  CATGTTTGGT  2160
AAAGTGATCT  ATTTCGCTGA  TCTTGTCTCC  AAGAGTGCCA  ACGACTGCCA  TACATCTTAG  2220
GAAGACCCAA  TAGGGTTAAT  CCTGTCGGAA  GAAGTTGCCC  TTGGAAACGT  GTGTGAACTG  2280
AAGCATGCTT  CACATATCAG  CAAGTTACCC  AAGGGCAAGC  ACAGTGTCAA  AGGTTTGGGC  2340
AAAACTACTC  CTGACCTTTC  AGCTAGTATC  CCACTGGATG  GTGTAGAGGT  TCCTCTTGGG  2400
ACCAGGGTTT  CATCTGGTGT  GAATGACACT  GTCTACTGTT  ATAATGAGTA  CATTGTCTAT  2460
GATATTGCTC  AGGTAAATCT  GAAATATCTG  CTGAAACTGA  AATTCAATTT  TAAGACCTCC  2520
TTGTGGTAAT  TGGGAGAGGT  GGCTGAGTCA  CACACGGTGA  CTCCTGGATT  AATTCACCCT  2580
AAGCGCTTCT  GCACCAACTC  ACCTGGCTGG  CTAAGTTGCT  GGTGGGTAGT  ACCTGTACTA  2640
```

AACCTCCTCA GAAAGGATTT TGCAGAAATG CATTAGAAGC TT                2682

( 2 ) INFORMATION FOR SEQ ID NO:4:

( i ) SEQUENCE CHARACTERISTICS:
        ( A ) LENGTH: 1592 base pairs
        ( B ) TYPE: nucleic acid
        ( C ) STRANDEDNESS: both
        ( D ) TOPOLOGY: linear ( i i ) MOLECULE TYPE: DNA ( x i ) SEQUENCE DESCRIPTION: SEQ ID NO:4:

AAGCTTGAAA AGGCCCTAAA GGCCCAGAAC GACCTGATCT GGAACATCAA GGACGAGCTA    60
ATGAAAGTGT GCTCTATTAA TGACCTGAAG GAGATGCTCA TCTTCAACAG GCAGCAGGTG   120
CCTTCCGGGG AGTCGGCGAT CTTGGACCGA GTAGCTGACA GCATGACGTT CGGTGCCCTC   180
CTTCCCTGTG AGGAATGCTC AGGTCAGCTG GTCTTCAAGA GCGACACTTA TTACTGCACC   240
GGGGACGTCA CGGCCTGGAC CAAGTGTATG GTCAAGACAT GGACACCCAA CCAGAAGGAA   300
TAGGTGATCC CACCGAGAAA TCTCTTAACT CAAGAAATTT AAGGTTAAAA AGCAGGACCG   360
TATATTTCCC CCAGAAACCA GTGACCCAGT GGCGGCCATG CCCCCACCCT CCACAGCCTC   420
CGAGCCTGCT GCCATGAACG CCTCTGCTCC AGCAGATAAG CCGTTATCCA ACATGAAGAT   480
CCTTACTCTT GGGAAGCTCT CCCGGAACAA GGATGAAGTG AAGGCCACGA TTGAGAAACT   540
CGGGGGAAAG TTGATGGGGA CGGCCAACAA GGCTTCTCCG TGCATCAGCA CTAAAGAGGA   600
GGTGGAAAAG AAGAAGAAGA AGATGGAGGA AGTGAAAGAA GCCCAACATC TGAGCTGTGT   660
CTGAGGACTT CCTCCAGGAC TTCTCTGCCT CCACAAGGGG CTCCAGGAGT TGTTCTCAGC   720
GCACATATTG ACCCCTGGG GGGCAGAGGT GAAGGCAGAG CCTGTTGAAG TCGTAGCCCC    780
AAGAGGGAAG TCGGTGGTGT CCCAGGGCAG CAGCGACTCT CAGATCCTGG ATCTCTCAAA   840
TCGCTTTTAC ATCCTGATCC CCACGACTT TGGGATGAAG GATCCTCTGC TCCTGAACAA    900
TGCAGACAGT GTGCAGGCCA AGGTAGAAAT GCTGGACAAC CTGCTGGACA TTGAGGTAGC   960
CTACGGTCTG CTCAGGGGAG GGTCTCACGA TAGCAGGAAG GACTCCATCG ATGTCAACTA  1020
TGAGAAGCTC AAAACTGACA TTAAGGTGGT TGACAGAGAT TCTGAAGAAG CTGAGATCAT  1080
CAGGAAGTAT GTTAAGAACA CTCATGCAAC CAACCACACA CGATGCATAT GACTTGGAAG  1140
TCATTGATAG CTTTAAGATA GAGTGTGAAG AGGAGTGCCA GCACTACAAG CCCTTTAAGC  1200
AGCTTCATAA CTGAAGGTTG CTGTGGCATG GGTCCAGGAC CACCAACTTT GCTGGGATCC  1260
TGTCCCTGGG TCTTTGGATA GCCTGCCTG AAGCACCTGT GATGGGCTAC ATGTTTGGTA   1320
AAGTGATCTA TTTCGCTGAT CTTGTCTCCA AGAGTGCCAA CGACTGCCAT ACATCTTAGG  1380
AAGACCCAAT AGGGTTAATC CTGTCGGAAG AAGTTGCCCT TGGAAACGTG TGTGAACTGA  1440
AGCATGCTTC ACATATCAGC AAGTTACCCA AGGGCAAGCA CAGTGTCAAA GGTTTGGGCA  1500
AAACTACTCC TGACCTTTCA GCTAGTATCC CACTGGATGG TGTAGAGGTT CCTCTTGGGA  1560
CCAGGGTTTC ATCTGGTGTG AATGACACCT GT                              1592

( 2 ) INFORMATION FOR SEQ ID NO:5:

( i ) SEQUENCE CHARACTERISTICS:
        ( A ) LENGTH: 3747 base pairs
        ( B ) TYPE: nucleic acid
        ( C ) STRANDEDNESS: both
        ( D ) TOPOLOGY: linear ( i i ) MOLECULE TYPE: DNA ( x i ) SEQUENCE DESCRIPTION: SEQ ID NO:5:

```
CTGCAGGGGG GGGGGGGGGG GGGGAATCTA TCAGGGAACG GCGGTAGGCC GGTAGCGGCG      60
TAGTTCGGTG GCGGCTCTGG CCGCTCAGGC CGTGCGGCTG GGATGAGCGC AACGCGAGGC     120
GGCGAGGCGG CAAGCGTGTT TCTAGGTCGT GGCGTCGGGC TTCCGGAGCT TTGGCGGCAG     180
CTAGGGGAGG ATGGCGGAGT CTTCGGATAA GCTCTATCGA GTCGAGTACG CCAAGAGCGG     240
GCGCGCCTCT TGCAAGAAAT GCAGCGAGAG CATCCCCAAG GACTCGCTCC GGATGGCCAT     300
CATGGTGCAG TCGCCCATGT TTGATGAAAA AGTCCCACAC TGGTACCACT TCTCCTGCTT     360
CTGGAAGGTG GGCCACTCCA TCCGGCACCC TGACGTTGAG GTGGATGGGT TCTCTGAGCT     420
TCGGTGGGAT GACCAGCAGA AAGTCAAGAA GACAGCGGAA GCTGGAGGAG TGACAGGCAA     480
AGGCCAGGAT GGAATTGGTA GCAAGGCAGA GAAGACTCTG GGTGACTTTG CAGCAGAGTA     540
TGCCAAGTCC AACAGAAGTA CGTGCAAGGG GTGTATGGAG AAGATAGAAA AGGGCCAGGT     600
GCGCCTGTCC AAGAAGATGG TGGACCCGGA GAAGCCACAG CTAGGCATGA TTGACCGCTG     660
GTACCATCCA GGCTGCTTTG TCAAGAACAG GGAGGAGCTG GGTTTCCGGC CCGAGTACAG     720
TGCGAGTCAG CTCAAGGGCT TCAGCCTCCT TGCTACAGAG GATAAAGAAG CCCTGAAGAA     780
GCAGCTCCCA GGAGTCAAGA GTGAAGGAAA GAGAAAAGGC GATGAGGTGG ATGGAGTGGA     840
TGAAGTGGCG AAGAAGAAAT CTAAAAAAGA AAAAGACAAG GATAGTAAGC TTGAAAAAGC     900
CCTAAAGGCT CAGAACGACC TGATCTGGAA CATCAAGGAC GAGCTAAAGA AGTGTGTTC     960
AACTAATGAC CTGAAGGAGC TACTCATCTT CAACAAGCAG CAAGTGCCTT CTGGGGAGTC    1020
GGCGATCTTG GACCGAGTAG CTGATGGCAT GGTGTTCGGT GCCCTCCTTC CTGCGAGGA    1080
ATGCTCGGGT CAGCTGGTCT TCAAGAGCGA TGCCTATTAC TGCACTGGGG ACGTCACTGC    1140
CTGGACCAAG TGTATGGTCA AGACACAGAC ACCCAACCGG AAGGAGTGGG TAACCCCAAA    1200
GGAATTCCGA GAAATCTCTT ACCTCAAGAA ATTGAAGGTT AAAAAGCAGG ACCGTATATT    1260
CCCCCCAGAA ACCAGCGCCT CCGTGGCGGC CACGCCTCCG CCCTCCACAG CCTCGGCTCC    1320
TGCTGCTGTG AACTCCTCTG CTTCAGCAGA TAAGCCATTA TCCAACATGA AGATCCTGAC    1380
TCTCGGGAAG CTGTCCCGGA ACAAGGATGA AGTGAAGGCC ATGATTGAGA AACTCGGGGG    1440
GAAGTTGACG GGGACGGCCA ACAAGGCTTC CCTGTGCATC AGCACCAAAA AGGAGGTGGA    1500
AAAGATGAAT AAGAAGATGG AGGAAGTAAA GGAAGCCAAC ATCCGAGTTG TGTCTGAGGA    1560
CTTCCTCCAG GACGTCTCCG CCTCCACCAA GAGCCTTCAG GAGTTGTTCT AGCGCACAT    1620
CTTGTCCCCT TGGGGGGCAG AGGTGAAGGC AGAGCCTGTT GAAGTTGTGG CCCCAAGAGG    1680
GAAGTCAGGG GCTGCGCTCT CCAAAAAAAG CAAGGGCCAG GTCAAGGAGG AAGGTATCAA    1740
CAAATCTGAA AAGAGAATGA AATTAACTCT TAAAGGAGGA GCAGCTGTGG ATCCTGATTC    1800
TGGACTGGAA CACTCTGCGC ATGTCCTGGA GAAAGGTGGG AAGGTCTTCA GTGCCACCCT    1860
TGGCCTGGTG GACATCGTTA AAGGAACCAA CTCCTACTAC AAGCTGCAGC TTCTGGAGGA    1920
CGACAAGGAA AACAGGTATT GGATATTCAG GTCCTGGGGC CGTGTGGGTA CGGTGATCGG    1980
TAGCAACAAA CTGGAACAGA TGCCGTCCAA GGAGGATGCC ATTGAGCAGT TCATGAAATT    2040
ATATGAAGAA AAACCGGGA ACGCTTGGCA CTCCAAAAAT TTCACGAAGT ATCCCAAAAA    2100
GTTTTACCCC CTGGAGATTG ACTATGGCCA GGATGAAGAG GCAGTGAAGA AGCTCACAGT    2160
AAATCCTGGC ACCAAGTCCA AGCTCCCCAA GCCAGTTCAG GACCTCATCA AGATGATCTT    2220
TGATGTGGAA AGTATGAAGA AAGCCATGGT GGAGTATGAG ATCGACCTTC AGAAGATGCC    2280
CTTGGGGAAG CTGAGCAAAA GGCAGATCCA GGCCGCATAC TCCATCCTCA GTGAGGTCCA    2340
GCAGGCGGTG TCTCAGGGCA GCAGCGACTC TCAGATCCTG GATCTCTCAA ATCGCTTTTA    2400
CACCCTGATC CCCCACGACT TTGGGATGAA GAAGCCTCCG CTCCTGAACA ATGCAGACAG    2460
```

```
TGTGCAGGCC  AAGGTGGAAA  TGCTTGACAA  CCTGCTGGAC  ATCGAGGTGG  CCTACAGTCT    2520
GCTCAGGGGA  GGGTCTGATG  ATAGCAGCAA  GGATCCCATC  GATGTCAACT  ATGAGAAGCT    2580
CAAAACTGAC  ATTAAGGTGG  TTGACAGAGA  TTCTGAAGAA  GCCGAGATCA  TCAGGAAGTA    2640
TGTTAAGAAC  ACTCATGCAA  CCACACACAG  TGCGTATGAC  TTGGAAGTCA  TCGATATCTT    2700
TAAGATAGAG  CGTGAAGGCG  AATGCCAGCG  TTACAAGCCC  TTAAGCAGC   TTCATAACCG    2760
AAGATTGCTG  TGGCACGGGT  CCAGGACCAC  CAACTTTGCT  GGGATCCTGT  CCCAGGGTCT    2820
TCGGATAGCC  CCGCCTGAAG  CGCCCGTGAC  AGGCTACATG  TTTGGTAAAG  GGATCTATTT    2880
CGCTGACATG  GTCTCCAAGA  GTGCCAACTA  CTACCATACG  TCTCAGGGAG  ACCCAATAGG    2940
CTTAATCCTG  TTGGGAGAAG  TTGCCCTTGG  AAACATGTAT  GAACTGAAGC  ACGCTTCACA    3000
TATCAGCAGG  TTACCCAAGG  GCAAGCACAG  TGTCAAGGT   TTGGGCAAAA  CTACCCCTGA    3060
TCCTTCAGCT  AACATTAGTC  TGGATGGTGT  AGACGTTCCT  CTTGGGACCG  GGATTTCATC    3120
TGGTGTGAAT  GACACCTCTC  TACTATATAA  CGAGTACATT  GTCTATGATA  TTGCTCAGGT    3180
AAATCTGAAG  TATCTGCTGA  AACTGAAATT  CAATTTTAAG  ACCTCCCTGT  GGTAATTGGG    3240
AGAGGTAGCC  GAGTCACACC  CGGTGGCTGT  GGTATGAATT  CACCCGAAGC  GCTTCTGCAC    3300
CAACTCACCT  GGCCGCTAAG  TTGCTGATGG  GTAGTACCTG  TACTAAACCA  CCTCAGAAAG    3360
GATTTACAG   AAACGTGTTA  AAGGTTTTCT  CTAACTTCTC  AAGTCCCTTG  TTTTGTGTTG    3420
TGTCTGTGGG  GAGGGGTTGT  TTTGGGGTTG  TTTTTGTTTT  TTCTTGCCAG  GTAGATAAAA    3480
CTGACATAGA  GAAAAGGCTG  GAGAGAGATT  CTGTTGCATA  GACTAGTCCT  ATGGAAAAAA    3540
CCAAAGCTTC  GTTAGAATGT  CTGCCTTACT  GGTTTCCCCA  GGGAAGGAAA  AATACACTTC    3600
CACCCTTTTT  TCTAAGTGTT  CGTCTTTAGT  TTTGATTTTG  GAAAGATGTT  AAGCATTTAT    3660
TTTTAGTTAA  AAATAAAAAC  TAATTTCATA  CTAAAAAAAA  AAAAAAAAA   AAAGTACCTT    3720
CTGAGGCGGA  AAGAACCAGC  CGGATCC                                           3747
```

( 2 ) INFORMATION FOR SEQ ID NO:6:

( i ) SEQUENCE CHARACTERISTICS:
        ( A ) LENGTH: 163 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Met  Ser  Trp  Arg  Lys  Val  Lys  Ala  Glu  Pro  Val  Glu  Val  Val  Ala  Pro
  1              5                  10                      15

Arg  Gly  Lys  Ser  Gly  Ala  Val  Leu  Ser  Lys  Lys  Ser  Lys  Gly  Gln  Val
                20                  25                      30

Lys  Glu  Glu  Gly  Ile  Asn  Lys  Ser  Glu  Lys  Arg  Met  Lys  Leu  Thr  Leu
            35                  40                  45

Lys  Gly  Gly  Ala  Ala  Val  Asp  Pro  Asp  Ser  Gly  Leu  Glu  His  Ser  Ala
        50                  55                  60

His  Val  Leu  Glu  Lys  Gly  Gly  Lys  Val  Phe  Ser  Ala  Thr  Leu  Ser  Leu
 65                  70                  75                      80

Val  Asp  Val  Val  Lys  Gly  Thr  Asn  Ser  Tyr  Tyr  Lys  Leu  Lys  Leu  Leu
                 85                  90                      95

Lys  Asp  Asp  Lys  Glu  Ser  Arg  His  Trp  Ile  Phe  Lys  Ser  Trp  Asp  Arg
                100                 105                     110

Val  Gly  Thr  Val  Ile  Gly  Ser  Asn  Lys  Leu  Glu  Gln  Met  Leu  Ser  Lys
             115                 120                 125

Glu  Asp  Thr  Ile  Glu  His  Phe  Met  Lys  Leu  Tyr  Glu  Glu  Lys  Leu  Gly
```

|  | 130 |  |  |  | 135 |  |  |  | 140 |  |  |
|---|---|---|---|---|---|---|---|---|---|---|---|
| Met | Leu | Gly | Thr | Pro | Lys | Ile | His | Lys | Val | Ser | Gln | Lys | Val | Leu | Pro |
| 145 |  |  |  |  | 150 |  |  |  |  | 155 |  |  |  |  | 160 |
| Pro | Gly | Asp |

( 2 ) INFORMATION FOR SEQ ID NO:7:

( i ) SEQUENCE CHARACTERISTICS:
        ( A ) LENGTH: 5345 base pairs
        ( B ) TYPE: nucleic acid
        ( C ) STRANDEDNESS: both
        ( D ) TOPOLOGY: linear ( i i ) MOLECULE TYPE: DNA ( x i ) SEQUENCE DESCRIPTION: SEQ ID NO:7:

```
TTTTAAGAAA GAACGTCCGG AATGGAAAAA GGAAGAAAAG GTAATCCCCA TTATGAGTTT      60
TAATGAGGAC TGGGAATCAG GGGTTCCTTC TAACCAGGTC CCACAAGGAA CCCTTCATAA     120
ACTTGAGAGT GGGACCCGAA GGGGAAAAAA TGACATTTTT GGTCGACACT GGAGTGGCTT     180
GCTCTTCCTT AATATACCCA CCAAGGGGCA CATACCCTCT AAGGAAAAGT AACAGTATC      240
AGAGTAAAAG GGGAGGGATT TCAAGTTCCA ATATTCAAGA AAATGTTAAT TAGGCAGGAA     300
TCAGAACCAA TTAAGGAGTC ACTCTTACAT GTTCCCAAAG CAGGAACTAA CCTCCTGGGT     360
TGAGACCTGA TTGTAGATTA GATTTAGCTT TAGGATTAGG AGTAGAGGAG GGACAAATAA     420
AACTAATGAT GGTTCTCCTA ACAGAGGAGG AAGAAGGTAA GATTAACTCC CTTTTGTGGG     480
TTAAGGAAGG CAACGGGAGG ATTAAAAAAT CACACCCTTA CAGACCGAAT GAAAACATCC     540
AGGAGAAAGA GTTTACAGGA GACAATATCC CATACCCATG AAGGGAGGAA AGGTCTCCAA     600
CCGGTAATAG AAGGACAAAT TAAAGACGAA CTATCGAGCT GGGTACTCGG GAGCCTGCGC     660
CAGGTGAGTG TGGGCGGGGC GGCAAGGCGG AAGCTCCAGG CGCAGGCGGC GGAAGCGCGT     720
GTCTCCAGGT CGTCGCGTCG GGCTCCTGGG ATTTGGCGGC AACTGTGGGA GGATGGCAGA     780
GTCCTCGGAT AAGCTCTACT GAGTGGAGTA CACCAAGAGC GGGCGCACCT CTTGCAAGAA     840
ATGCAGCGAG AGCATCCCCA AGGACTCGCT CCGGATGGCC ATCATGGTGC AATAGTCCAT     900
GTTGATGGAG AAGTCCCACA CTGGTACCAC TTCTCCTGCT TGCAGAAGGT GGGCCACTCC     960
ATGCGGCACC CTGACGTTGA GGTGGATGGA TTCTCTGAGC TTTGGTGGGA TGACCAGCAG    1020
AAAGTCAAGA AGACACGTGA CGCTGGAGGA GTGACGGGCA AGGCCAGAA TGGAATTGGT     1080
AGCAAGGCAG AGAAGACGCT GGGTGACTTT GCAGCAGAGT AGGCCAAGTC AGCAGAAGC     1140
AAGTGCAAGA GGTGTTATGG AGAAGATAGA AAAGGGCCAG ATGCGCCTAT CCAAGAAGAT    1200
GCTGGACCCT GAGAAGCCTC AGCTAGGCAT GATTGACCCC TGGTACCACC CAGGCTGCTT    1260
TGTCAAGAAC AGGGAGGAGC TGGGTTTCCA GCCTGAGTAC AGTGCGAGTC AGCTCAAGGG    1320
CTTCAGCCTC CTCGCTGCAG AGGATAAAGA AACCCTGAAG AAGCAGCTCC AGGAGTCAA     1380
GAGTGAAGGA AAGAGAGAAG GCGATGAGGT GGATGGAGTG GATGAAGTGG CCAAGAAGAA    1440
ATCTAAAAAA AAAAAAAAAC GAGGATAATA AGCTTGAAAA GGCCCTAAAG CCCAGAACG     1500
ACCTGATCTG GAACATCAAG GACGAGCTAA TGAAAGTGTG CTCTATTAAT GACCTGAAGG    1560
AGATGCTCAT CTTAACAGG CAGCAGGTGC CTTCGGGGA GTCGGCGATC TTGGACCGAG      1620
TAGCTGACAG CATGACGTTC GGTGCCCTCC TTCCCTGTGA GGAATGCTCA GGTCAGCTGG    1680
TCTTCAAGAG CGACACTTAT TACTGCACCG GGACGTCAC GGCCTGGACC AAGTGTATGG     1740
TCAAGACATG GACACCCAAC CAGAAGGAAT AGGTGATCCC ACCGAGAAAT CTCTTAACTC    1800
AAGAAATTTA AGGTTAAAAA GCAGGACCGT ATATTTCCCC CAGAAACCAG TGACCCAGTG    1860
```

```
GCGGCCATGC CCCCACCCTC CACAGCCTCC GAGCCTGCTG CCATGAACGC CTCTGCTCCA    1920
GCAGATAAGC CGTTATCCAA CATGAAGATC CTTACTCTTG GAAGCTCTC  CCGGAACAAG    1980
GATGAAGTGA AGGCCACGAT TGAGAAACTC GGGGGAAAGT TGATGGGGAC GGCCAACAAG    2040
GCTTCTCCGT GCATCAGCAC TAAAGAGGAG GTGGAAAAGA AGAAGAAGAA GATGGAGGAA    2100
GTGAAAGAAG CCAACATCTG AGCTGTGTCT GAGGACTTCC TCCAGGACTT CTCTGCCTCC    2160
ACCAAGGGGC TCCAGGAGTT GTTCTCAGCG CACATATTGA CCCCTGGGG  GGCAGAGGTG    2220
AAGGCAGAGC CTGTTGAAGT CGTAGCCCCA AGAGGGAAGT CAGGAGCTGT GCTCTCCAAA    2280
AAAAGCAAGG GCCAGGTCAA GGAGGAAGGT ATCAACAAAT CTGAAAAGAG AATGAAATTA    2340
ACTCTTAAAG GAGGAGCAGC TGTGGATCCT GACTCTGGTC TGGAACACTC TGCGCATGTC    2400
CTGGAGAAAG GTGAAGGCAG AGCCTGTTGA AGTCGTAGCC CAAGAGGGA  AGTCAGGAGC    2460
TGTGCTCTCC AAAAAAAGCA AGGGCCAGGT CAAGGAGGAA GGTATCAACA AATCTGAAAA    2520
GAGAATGAAA TTAACTCTTA AAGGAGGAGC AGCTGTGGAT CCTGACTCTG GTCTGGAACA    2580
CTCTGCACAT GTTCTGGAGA AAGGTGGGAA GGTCTTCAGT GCCACCCTCA GCCTGGTGGA    2640
CGTCGTTAAA GGAACCAACT CCTATTACAA GCTGAAGTTG CTGAAGGATG ACAAGGAAAG    2700
CAGGCATTGG ATATTCAAGT CCTGGGACCG TGTGGGCACG GTGATCGGTA GCAACAAACT    2760
GGAACAGATG CTGTCCAAGG AGGACACCAT TGAACACTTC ATGAAATTAT ATGAAGAAAA    2820
ACTAGGAATG CTTGGCACTC CAAAAATTCA CAAAGTATCC CAAAAGTTC  TACCCCCTGG    2880
AGATTGACTA CGGCCAGGAC AAAGAGGCGG TGAAGAAGCC GACAGTAAAT CCTGGCACCA    2940
AGTCCATGCT CCCCAAGCCA GTTCAGGACC TCATCAAGAT GATCTTTGAT GTGGAAAGTA    3000
TGAGCAAAGC CATGGTGGGG TGTGAGATCA ACCTTCAGAT GCCCTTGGGG AAGCTGAGCA    3060
AAAGGCAAAT CCAGGCCGCG TACTCCATCC TCAGGTCCAG CAGGTGGTGT CCCAGGGCAG    3120
CAGCGACTCT CAGATCCTGG ATCTCTCAAA TCGCTTTTAC ATCCTGATCC CCACGACTT     3180
TGGGATGAAG GATCCTCTGC TCCTGAACAA TGCAGACAGT GTGCAGGCCA AGGTAGAAAT    3240
GCTGGACAAC CTGCTGGACA TTGAGGTAGC CTACGGTCTG CTCAGGGGAG GTCTCACGA     3300
TAGCAGGAAG GACTCCATCG ATGTCAACTA TGAGAAGCTC AAAACTGACA TTAAGGTGGT    3360
TGACAGAGAT TCTGAAGAAG CTGAGATCAT CAGGAAGTAT GTTAAGAACA CTCATGCAAC    3420
CAACCACACA CGATGCATAT GACTTGGAAG TCATTGATAG CTTTAAGATA GAGTGTGAAG    3480
AGGAGTGCCA GCACTACAAG CCCTTTAAGC AGCTTCATAA CTGAAGGTTG CTGTGGCATG    3540
GGTCCAGGAC CACCAACTTT GCTGGGATCC TGTCCCTGGG TCTTTGGATA GCCCTGCCTG    3600
AAGCACCTGT GATGGGCTAC ATGTTTGGTA AAGTGATCTA TTTCGCTGAT CTTGTCTCCA    3660
AGAGTGCCAA CGACTGCCAT ACATCTTAGG AAGACCCAAT AGGGTTAATC CTGTCGGAAG    3720
AAGTTGCCCT TGGAAACGTG TGTGAACTGA AGCATGCTTC ACATATCAGC AAGTTACCCA    3780
AGGGCAAGCA CAGTGTCAAA GGTTTGGGCA AAACTACTCC TGACCTTTCA GCTAGTATCC    3840
CACTGGATGG TGTAGAGGTT CCTCTTGGGA CCAGGGTTTC ATCTGGTGTG AATGACACCT    3900
GTCTACTGTA TAATGAGTAC ATTGTCTATG ATATTGCTCA GGTAAATCTG AAATATCTGC    3960
TGAAACTGAA ATTCAATTTT AAGACCTCCT TGTGGTAATT GGGAGAGGTG GCTGAGTCAC    4020
ACACGGTGAC TCTGGTATTA ATTCACCCTA AGCGCTTCTG CACCAACTCA CCTGGCTGGC    4080
TAAGTTGCTG GTGGGTAGTA CCTGTACTAA ACCTCCTCAG AAAGGATTTT GCAGAAATGC    4140
ATTAGAAGCT TTTTCCCAAA TTTTTAGTC  TCTTGTTTTG TGTTGTGTTT GTGGGGAGGG    4200
GTTGTTTTTG TTTTTCTTG  CCAGGTAGAT AAAACTGACA AGCTGGAGAG AGATTCTGTT    4260
TGCATGGATT AGTCCTCTGG AAAAAACCAA GCTGTGCTAC AATATCTGCC TTAGTGGTTT    4320
```

-continued

| | | | | | | |
|---|---|---|---|---|---|---|
| CCCCAGGGAA | GAAAAATAT | GTTTCCACCC | TTTTTTTTG | TTTGTTTGTC | TTTAGTTTTG | 4380 |
| ATTTTGGAAA | GATGTTAAGC | ATTTATTTTT | AGTTAAAAAT | AAAAATTGAT | TTCATACTAA | 4440 |
| AAAAAAAGAT | GGGTTATTGA | AACCCTGTAT | GTCACCATAC | AATACTCCAG | TTCTCCCAGT | 4500 |
| AAAGAAACCA | GATGGGTCAT | ACAGATTAGT | GCAAATCTA | AGGTCTATAC | ATAAAATTGT | 4560 |
| CCAAACTTGA | CATCTTGTGG | TGCCTAACCC | CTACACCCAC | CTTAATAAAA | TACTCTATAA | 4620 |
| ACATAAGTGG | TTCAGCATAG | TGGATCTGAA | AGATGCATTC | TGGCCATGTC | CCCTAGACTC | 4680 |
| TAAGAGTAGG | GACCTCTTTG | CCTTTGAATG | AAAAACCTCA | TAACTGGGAG | AAAGCAGAGG | 4740 |
| TATCACTGGA | CTGTGCTGCC | ACAAGTTTTC | ACGGAAGCCC | CAAACTTACT | TGGTCAAGTC | 4800 |
| TTAGAAAAG | TTCTGGAGGA | ATTCCAACCA | TCCAAAGAAA | CCCAGCTGTT | ACAATATGTG | 4860 |
| GATGATCTTC | TAATTCTGG | GGAAGGAGG | GCCGAGGTAT | CAGAAGCCAC | CATAAGCTTA | 4920 |
| CTTAATTTCC | TAGGGGAAAA | GGGTTTGCGA | GTCTCCAAAA | CCAAATCGCA | ATTTGTAGGA | 4980 |
| GAAGTTAAAT | ATTTAGGACA | CCTAATTAGT | GAAGGAAAGC | AGAGAATAAA | CGCAGAGAGA | 5040 |
| ATATCGGGAA | TAGTGGGTCT | GCCCTTGCCT | AAGACAAAGA | GAGAACTCCA | AAACTTTTA | 5100 |
| GGTTTAACTG | GCTACTGTAG | GTTATGGATG | GACTCATATG | TTCAAAGGAC | AAAGATTCTG | 5160 |
| TATTTAAGT | TACTAAAAAG | GGAACCCAAC | CCCTTGCAAA | GGTCCCCAGA | AGAAATTAAG | 5220 |
| GCAGTGGAGG | ATTTAAAGCA | AGCCCTCACA | CAGCCCAGT | CCTGGCCCTC | CTATCTTTAA | 5280 |
| ATAAAACGTT | TCATCTGTCT | GTAACAGACC | AGGCCCTTGG | GGTGCTCATT | CAAACCTGGT | 5340 |
| GGGGT | | | | | | 5345 |

What is claimed is:

1. An isolated nucleic acid molecule consisting of a nucleotide sequence selected from the group consisting of SEQ ID Nos. 1 and 2 and optionally carrying a label.

2. A method for detecting the presence or absence of a human DNA polymorphism associated with a predisposition for cancer, wherein said polymorphism is a deletion of about 200 base pairs of the pseudogene for poly (ADP-ribose) polymerase on human chromosome 13, and wherein said method comprises the steps of
    (a) contacting a sample containing nucleic acid from a human with one or more allele specific amplification primers capable of hybridizing to regions flanking said polymorphism, wherein the sequences of said primers are derived from sequences which flank a region which differs in size between the two alleles of the pseudogene for poly (ADP-ribose) polymerase on human chromosome 13, and wherein said allele specific amplification primers amplify sequences from human chromosome 13 but do not amplify sequences from human chromosomes 1 or 14;
    (b) amplifying sequences of nucleic acid within said sample;
    (c) amplifying sequences of a cloned nucleic acid derived from the A allele of the pseudogene for poly (ADP-ribose) polymerase on human chromosome 13 with the allele specific amplification primers of step (a), wherein said A allele lacks said deletion of about 200 base pairs; and
    (d) determining the sizes of the amplified sequences from steps (b) and (c) via electrophoresis, wherein the presence of amplified sequences resulting from step (b) that are smaller in size by about 200 base pairs than the amplified sequences resulting from step (c) indicates that said polymorphism associated with cancer is present in said sample.

3. The method of claim 2 wherein said allele specific amplification primers are selected from the group consisting of SEQ. ID NO. 1 and SEQ) ID NO. 2.

4. The method of claim 2 wherein the nucleotide sequence said allele specific amplification primers are sequences of the human chromosome 13 pseudogene for poly (ADP-ribose) polymerase, SEQ ID NO. 3 or SEQ ID NO. 4 but are not sequences of the human chromosome 1 poly (ADP-ribose) polymerase gene SEQ ID NO. 5.

5. The method of claim 2 wherein said cancer is selected from the group consisting of Burkitt's lymphoma, B follicular cell lymphoma, small cell lung carcinoma, colon-rectal carcinoma and breast adenocarcinoma.

6. An isolated DNA molecule consisting of the nucleotide sequence of SEQ ID NO. 3 optionally carrying a label.

7. An isolated DNA molecule consisting of the nucleotide sequence of SEQ ID NO. 4 optionally carrying a label.

8. An allele specific primer consisting of SEQ ID NO. 3 sequences which flank a region which differs in size between the two alleles of the pseudogene for poly (ADP-ribose) polymerase on human chromosome 13, said allele specific primer optionally carrying a label, and wherein said. allele specific amplification primer amplifies sequences from human chromosome 13 but does not amplify sequence from human chromosomes 1 or 14.

* * * * *